(12) United States Patent
Colby et al.

(10) Patent No.: US 6,342,380 B1
(45) Date of Patent: Jan. 29, 2002

(54) GERMACRENE C SYNTHASE GENE OF LYCOPERSICON ESCULENTUM

(75) Inventors: Sheila M. Colby, Sunnyvale, CA (US); John E. Crock, Moscow, ID (US); Peggy G. Lemaux, Moraga, CA (US); Rodney B. Croteau, Pullman, WA (US)

(73) Assignees: The Regents of the University of California, Berkley, CA (US); Washington State Research Foundation, Pullman, WA (US)

( * ) Notice: Subject to any disclaimer, the term of this patent is extended or adjusted under 35 U.S.C. 154(b) by 0 days.

(21) Appl. No.: 09/601,091
(22) PCT Filed: Feb. 2, 1999
(86) PCT No.: PCT/US99/02133
§ 371 Date: Sep. 19, 2000
§ 102(e) Date: Sep. 19, 2000
(87) PCT Pub. No.: WO99/38957
PCT Pub. Date: Aug. 5, 1999

Related U.S. Application Data
(60) Provisional application No. 60/073,579, filed on Feb. 2, 1998.

(51) Int. Cl.[7] .............................. C12N 9/00; C12N 5/04; C12P 21/06; C07H 21/04
(52) U.S. Cl. ...................... 435/183; 435/69.1; 435/419; 536/23.2
(58) Field of Search ................................. 435/183, 69.1, 435/419; 536/23.2

(56) References Cited

FOREIGN PATENT DOCUMENTS

| WO | WO 95/11913 | * | 5/1995 |
| WO | WO 96/36697 | * | 11/1996 |
| WO | WO 97/38571 | * | 10/1997 |

OTHER PUBLICATIONS

Colby Sheila M. et al, Germacrene C synthase from *Lycopersicon esculentum* cv. VFNT Cherry tomato: cDNA isolation, characterization, and bacterial expression of the multiple product sequiterpene cyclase, Proc. Natl. Acad. Sci. USA, 1998, 95, 2216–2221.*
Crock John et al, Isolation and bacterial expression of a sesquiterpene synthase cDNA clone from peppermint (*Mentha x piperita*, L.) that produces the aphid alarm pheromone (E)–beta–farnesene, Proc. Natl. Acad. Sci. USA, 1997, 94, 12833–12838.*
Starks Courtney M. et al, Structural Basis for Cyclic Terpene Biosynthesis by Tobacco 5–Epi–Aristolochene Synthase, Science, 1997, 277, 1815–1820.*
Back Kyoungwhan et al, Cloning and Bacterial Expression of a Sesquiterpene Cyclase from *Hoyscyamus muticus* and Its Molecular Comparison to Related Terpene Cyclases, J. Biol. Chem. 1995, 270, 7375–7381.*
Chen Xiao–Ya et al, Cloning, Expression and Characterization of (+)– delta–Cadinene Synthase: a Catalyst for Cotton Phytoalexin Biosynthesis, Arch. Biochem. Biophys. 1995, 324, 255–266.*
Chen Xiao–Ya et al, Cloning and Heterologous Expression of a Second (+)– delta–Caninene Synthase from *Gossypium arboreum*, J. Nat. Prod. 1996, 59, 944–951.*

* cited by examiner

*Primary Examiner*—Ponnathapu Achutamurthy
*Assistant Examiner*—Malgorzata A. Walicka
(74) *Attorney, Agent, or Firm*—Klarquist Sparkman, LLP

(57) ABSTRACT

Germacrene C synthase genes from *Lycopersicon esculentum* have been cloned and sequenced. Transgenic expression of germacrene C synthase in plants can result in beneficial and useful characteristics such as increased host resistance to pathogens and herbivores and altered flavor and odor profiles.

10 Claims, 11 Drawing Sheets

FIG. 4

```
  1  MAASSADKCR  PLANFHPSVW  GYHFLSYTHE  ITNQEKVEVD  EYKETIRKML
 51  VETCDNSTQK  LVLIDAMQRL  GVAYHFDNEI  ETSIQNIFDA  SSKQNDNDNN
101  LYVVSLRFRL  VRQQGHYMSS  DVFKQFTNQD  GKFKETLTND  VQGLLSLYEA
151  SHLRVRNEEI  LEEALTFTTT  HLESIVSNLS  NNNNSLKVEV  GEALTQPIRM
201  TLPRMGARKY  ISIYENNDAH  HHLLLKFAKL  DFNMLQKFHQ  RELSDLTRWW
251  KDLDFANKYP  YARDRLVECY  FWILGVYFEP  KYSRARKMMT  KVLNLTSIID
301  DTFDAYATFD  ELVTFNDAIQ  RWDANAIDSI  QPYMRPAYQA  LLDIYSEMEQ
351  VLSKEGKLDR  VYYAKNEMKK  LVRAYFKETQ  WLNDCDHIPK  YEEQVENAIV
401  SAGYMMISTT  CLVGIEEFIS  HETFEWLMNE  SVIVRASALI  ARAMNDIVGH
451  EDEQERGHVA  SLIECYMKDY  GASKQETYIK  FLKEVTNAWK  DINKQFFRPT
501  EVPMFVLERV  LNLTRVADTL  YKEKDTYTNA  KGKLKNMINS  ILIESVKI*
```

FIG. 6

```
   1 gaagcttgaa aaaaagcaaa ccttagaaca aacaagcaat ggctgcttct tctgctgata
  61 agtgtcgccc cttggctaat tttcacccat ctgtttgggg atatcatttc ctttcttata
 121 ctcatgaaat tactaatcaa gaaaaagttg aagttgatga gtacaaagag acaattagaa
 181 aaatgctggt ggaaacttgc gacaatagca ctcaaaagct tgtgttgata gacgcgatgc
 241 aacgattggg agtggcttat catttcgata tgaaattgaa acatccatt caaaacattt
 301 ttgatgcatc gtccaaacag aatgataatg acaacaacct ttacgttgtg tctcttcgtt
 361 ttcgacttgt gaggcaacaa ggccattaca tgtcttcaga tgtgttcaag caattcacca
 421 accaagatgg gaaattcaag gaaacactta ctaatgatgt ccaaggatta ttgagtttgt
 481 atgaagcatc acatctgaga gtgcgtaatg aggagattct tgaagaagct cttacattta
 541 ccaccactca tctcgagtct attgtctcca acttgagcaa taataataac tctcttaagg
 601 ttgaagttgg tgaagcctta actcagccta ttcgcatgac tttaccaagg atgggagcta
 661 gaaaatacat atccatttac gaaaacaatg atgcacacca ccatttgctt ttgaaatttg
 721 ctaaattgga ttttaacatg ctgcaaaagt ttcaccaaag agcttagt gatcttacaa
 781 ggtggtggaa agatttggat tttgcaaata aatatccata tgcaagagac aggttggttg
 841 agtgttactt ctggatatta ggagtgtatt ttgagccaaa atatagtcgt gcgagaaaaa
 901 tgatgacaaa agtactcaac ctgacctcca ttattgacga cactttgat gcttatgcaa
 961 cctttgacga acttgtgact ttcaatgatg caatccagag atgggatgct aatgcaattg
1021 attcaataca accatatatg agacctgctt atcaagctct tctagacatt tacagtgaaa
1081 tggaacaagt gttgtccaaa gaaggtaaac tggaccgtgt atactatgca aaaaatgaga
1141 tgaaaaagtt ggtgagagcc tattttaagg aaacccaatg gttgaatgat tgtgaccata
1201 ttccaaaata tgaggaacaa gtggagaatg caatcgtaag tgctggctat atgatgatat
1261 caacaacttg cttggtcggt atagaagaat ttatatccca cgagactttt gaatggttga
1321 tgaatgagtc tgtgattgtt cgagcttccg cattgattgc cagagcaatg aacgatattg
1381 ttggacatga agatgaacaa gaaagaggac atgtagcttc acttattgaa tgttacatga
1441 agattatgg agcttcaaag caagagactt acattaagtt cctgaaagag gtcaccaatg
1501 catggaagga cataaacaaa caattcttcc gtccaactga agtaccaatg tttgtccttg
1561 aacgagttct aaatttgaca cgtgtggctg acacgttata taagagaaa gatacatata
1621 caaacgccaa aggaaaactt aaaaacatga ttaattcaat actaattgaa tctgtcaaaa
1681 tataaatata atgctgaaat tgcaccttca tcattcaact attcacagca aataaggca
1741 tataataaat tgaagactca caacatatga gttgttaatt cctgggatgt ttgaaataaa
1801 caataattgt ttttatttaa tttgctaagc aaaagtgaaa tatcaacac ttgagttgta
1861 ttaaaaaaaa aaaaaaaaa
```

FIG. 7

MAASSADKCRPLANFHPSVWGYHFLSYTHEITNQEKVEVDEYKE
TIRKMLVETCDNSTQKLVLIDAMQRLGVAYHFDNEIETSIQNIFDASSKQNDNDNNLY
VVSLRFRLVRQQGHYMSSDVFKQFTNQDGKFKETLTNDVQGLLSLYEASHLRVRNEEI
LEEALTFTTTHLESIVSNLSNNNNSLKVEVGEALTQPIRMTLPRMGARKYISIYENND
AHHHLLLKFAKLDFNMLQKFHQRELSDLTRWWKDLDFANKYPYARDRLVECYFWILGV
YFEPKYSRARKMMTKVLNLTSIIDDTFDAYATFDELVTFNDAIQRWDANAIDSIQPYM
RPAYQALLDIYSEMEQVLSKEGKLDRVYYAKNEMKKLVRAYFKETQWLNDCDHIPKYE
EQVENAIVSAGYMMISTTCLVGIEEFISHETFEWLMNESVIVRASALIARAMNDIVGH
EDEQERGHVASLIECYMKDYGASKQETYIKFLKEVTNAWKDINKQFFRPTEVPMFVLE
RVLNLTRVADTLYKEKDTYTNAKGKLKNMINSILIESVKI

FIG. 8A

```
   1 AAAAAAAGCC AAACCTTAGA ACAAACAAGC AATGGCTGCT TCTTCTGCTG
  51 ATAAGTGTCG CCCCTTGGCT AATTTTCACC CATCTGTTTG GGGATATCAT
 101 TTCCTTTCTT ATACTCATGA AATTACTAAT CAAGAAAAAG TTGAAGTTGA
 151 TGAGTACAAA GAGACAATTA GAAAATGCT GGTGGAAACT TGCGACAATA
 201 GCACTCAAAA GCTTGTGTTG ATAGACGCGA TGCAACGATT GGGAGTGGCT
 251 TATCATTTCG ATAATGAAAT TGAAACATCC ATTCAAAACA TTTTTGATGC
 301 ATCGTCCAAA CAGAATGATA ATGACAACAA CCTTTACGTT GTGTCTCTTC
 351 GTTTTCGACT TGTGAGGCAA CAAGGCCATT ACATGTCTTC AGATGTGTTC
 401 AAGCAATTCA CCAACCAAGA TGGGAAATTC AAGGAAACAC TTACTAATGA
 451 TGTCCAAGGA TTATTGAGTT TGTATGAAGC ATCACATCTG AGAGTGCGTA
 501 ATGAGGAGAT TCTTGAAGAA GCTCTTACAT TTACCACCAC TCATCTCGAG
 551 TCTATTGTCT CCAACTTGAG CAATAATAAT AACTCTCTTA AGGTTGAAGT
 601 TGGTGAAGCC TTAACTCAGC CTATTCGCAT GACTTTACCA AGGATGGGAG
 651 CTAGAAAATA CATATCCATT TACGAAAACA ATGATGCACA CCACCATTTG
 701 CTTTTGAAAT TGCTAAATT GGATTTTAAC ATGCTGCAAA AGTTTCACCA
 751 AAGAGAGCTT AGTGATCTTA CAAGGTGGTG AAAGATTTG GATTTTGCAA
 801 ATAAATATCC ATATGCAAGA GACAGGTTGG TTGAGTGTTA CTTCTGGATA
 851 TTAGGAGTGT ATTTTGAGCC AAAATATAGT CGTGCGAGAA AAATGATGAC
 901 AAAAGTACTC AACCTGACCT CCATTATTGA CGACACTTTT GATGCTTATG
 951 CAACCTTTGA CGAACTTGTG ACTTTCAATG ATGCAATCCA GAGATGGGAT
1001 GCTAATGCAA TTGATTCAAT ACAACCATAT ATGAGACCTG CTTATCAAGC
1051 TCTTCTAGAC ATTTACAGTG AAATGGAACA AGTGTTGTCC AAAGAAGGTA
1101 AACTGGACCG TGTATACTAT GCAAAAAATG AGATGAAAAA GTTGGTGAGA
1151 GCCTATTTTA AGGAAACCCA ATGGTTGAAT GATTGTGACC ATATTCCAAA
1201 ATATGAGGAA CAAGTGGAGA ATGCAATCGT AAGTGCTGGC TATATGATGA
1251 TATCAACAAC TTGCTTGGTC GGTATAGAAG AATTTATATC CCACGAGACT
1301 TTTGAATGGT TGATGAATGA GTCTGTGATT GTTCGAGCTT CCGCATTGAT
1351 TGCCAGAGCA ATGAACGATA TTGTTGGACA TGAAGATGAA CAAGAAAGAG
```

DNA sequence of tomato cDNA clone 14.2

FIG. 8B

```
1401 GACATGTAGC TTCACTTATT GAATGTTACA TGAAAGATTA TGGAGCTTCA
1451 AAGCAAGAGA CTTACATTAA GTTCCTGAAA GAGGTCACCA ATGCATGGAA
1501 GGACATAAAC AAACAATTCT CCCGTCCAAC TGAAGTACCA ATGTTTGTCC
1551 TTGAACGAGT TCTAAATTTG ACACGTGTGG CTGACACGTT ATATAAGGAG
1601 AAAGATACAT ATTCAACCGC CAAAGGAAAA CTTAAAAACA TGATTAATCC
1651 AATACTAATT GAATCTGTCA AAATATAAAT ATAATGCTGA AATTGCACCT
1701 TCATCATCCA ACTATTCACA GCAAATAAG GCATATAATA AATTGAAGAC
1751 TCACAACATA TGAGTTGTTA ATTCCTGGGA TGTTTGAAAT AAACAATAAT
1801 TGTTTTTATT TAATTTGCTA AGCCAAAGTG AAATATACAA CACTTGAGTT
1851 GTATTAAATC ATGTTTTATC TCATTTCCAG CTTGTGAGTT TGGATTATTA
1901 TATTGTTAAT TATCATCACT TTATAATGTA CTGTAATCGT ATTGTATTTG
1951 TATTGTAGTG TTGTCATAAT AAAATTTGAA TAAAATATAT TTTTGTTTCA
2001 ATTCCAAAAA AAAAAAAAA AAAA
```

FIG. 9

Deduced amino acid sequence of the protein coding region of cDNA clone 14.2

```
  1 MAASSADKCR PLANFHPSVW GYHFLSYTHE ITNQEKVEVD EYKETIRKML
 51 VETCDNSTQK LVLIDAMQRL GVAYHFDNEI ETSIQNIFDA SSKQNDNDNN
101 LYVVSLRFRL VRQQGHYMSS DVFKQFTNQD GKFKETLTND VQGLLSLYEA
151 SHLRVRNEEI LEEALTFTTT HLESIVSNLS NNNNSLKVEV GEALTQPIRM
201 TLPRMGARKY ISIYENNDAH HHLLLKFAKL DFNMLQKFHQ RELSDLTRWW
251 KDLDFANKYP YARDRLVECY FWILGVYFEP KYSRARKMMT KVLNLTSIID
301 DTFDAYATFD ELVTFNDAIQ RWDANAIDSI QPYMRPAYQA LLDIYSEMEQ
351 VLSKEGKLDR VYYAKNEMKK LVRAYFKETQ WLNDCDHIPK YEEQVENAIV
401 SAGYMMISTT CLVGIEEFIS HETFEWLMNE SVIVRASALI ARAMNDIVGH
451 EDEQERGHVA SLIECYMKDY GASKQETYIK FLKEVTNAWK DINKQFSRPT
501 EVPMFVLERV LNLTRVADTL YKEKDTYSTA KGKLKNMINP ILIESVKI*
```

GERMACRENE C SYNTHASE GENE OF *LYCOPERSICON ESCULENTUM*

CROSS REFERENCE TO RELATED APPLICATION

This application is a 371 of the application PCT/US99/02133 filed Feb. 2, 1999 and corresponds to U.S. provisional application No. 60/073,579, filed on Feb. 2, 1998.

ACKNOWLEDGMENT OF GOVERNMENT SUPPORT

This invention was made with government support under U.S. Department of Agriculture NRI Grant 93-37301-9504, U.S. Department of Agriculture ARC Contingency Funds for Whitefly Research, and National Institutes of Health Grant GM31354. The government has certain rights in this invention.

TECHNICAL FIELD

This invention is related to germacrene C synthase genes and related compositions and methods.

BACKGROUND ART

Volatile metabolites of Lycopersicon species are of interest because of their roles in tomato flavor and in host defense, for example against plant pathogens, e.g., microbial pathogens, and pests, e.g., arthropod and mammalian herbivores (Buttery et al., *ACS Symp. Ser.* 52:22–34, 1993; Buttery et al., *J. Agric. Food Chem.* 38:2050–2053, 1990; Carter et al., *J. Agric. Food Chem.* 37:1425–1428, 1989; Lin et al., *J. Chem. Ecol.* 13:837–850, 1987; and Carter et al., *J. Agric. Food Chem.* 37:206–210, 1989). Whereas few volatile terpenoids are found in fruit (Buttery et al., *ACS Symp. Ser.* 52:22–34, 1993; and Buttery et al., *J. Agric. Food Chem.* 38:2050–2053, 1990), the leaf glandular trichomes produce a rich spectrum of monoterpenes and sesquiterpenes. Nearly twenty monoterpenes, including limonene, have been found in the leaves of the domestic tomato *L. esculentum* (Buttery et al., *J. Agric. Food Chem.* 35:1039–1042, 1987; and Lundgren et al., *Nord. J. Bot.* 5:315–320, 1985), and most are also present in wild tomato species (Lundgren et al., *Nord. J. Bot.* 5:315–320, 1985). A number of C13 norsesquiterpenoid glycosidic ethers have been reported in tomato fruit (Marlatt et al., *J. Agric. Food Chem.* 40:249–252, 1992); these compounds are derived by degradation of carotenoids (Isoe et al., *Helv. Chim. Acta* 56:1514–1516, 1973). The sesquiterpene content of tomato leaf oil varies considerably among species, with caryophyllene and humulene being widespread and reported from *L. esculentum, L. hirsutum, L. pimpinellifolium, L. peruvianum, L. cheesmanii, L. chilense* and *L. chumielewski* (Lundgren et al., *Nord. J. Bot.* 5:315–320, 1985). The epoxides of both of these sesquiterpenes are also present in *L. esculentum*, as is a low level of δ-elemene (Buttery et al., *J. Agric. Food Chem.* 35:1039–1042, 1987). Various accessions of *L. hirsutum* contain α-copaene, γ-elemene, zingiberene and α-santalene as major leaf oil sesquiterpenes (Lundgren et al., *Nord. J. Bot.* 5:315–320, 1985). Germacrenes have not been reported in the genus Lycopersicon.

The terpenoid composition of the highly disease resistant *L. esculentum* cv. 'VFNT Cherry' (a tomato of multi-species pedigree carrying resistance to *Verticillium dahliae, Fusarium oxysporum*, root-knot Nematode, Tobacco mosaic virus and Alternaria stem canker) has not been examined, although it is an important breeding line (Jones et al., *HortSci.* 15:98, 1980).

SUMMARY OF THE INVENTION

A germacrene C synthase gene from *Lycopersicon esculentum* has been cloned and sequenced. Transgenic expression of this gene in cells of a plant results in, for example, increased resistance to pathogens. Such pathogens include, for example, viruses, bacteria, spots, wilts, rusts, mildews, and related fungi as well as nematodes. Transgenic expression also will alter flavor and odor profile, which will deter eating of the plants by herbivores, such as Coleopteran, Lepidopteran, Homopteran, Heteropteran, and Dipteran pests, as well as acarine plant mites and related arthropods, mollusks, and mammalian herbivores. Additionally, expression of germacrene C synthase may increase the neutraceutical value of the plant and may also enhance the plant's attractiveness for pollinators, and possible for insect predators.

The invention includes a purified protein having a primary amino acid sequence as shown in FIG. 4 (SEQ ID NO:2). This protein displays germacrene C synthase biological activity as described herein.

Also encompassed within the invention are proteins with a primary amino acid sequence that differs from the sequence as shown in FIG. 4 (SEQ ID NO:2) only by one or more conservative amino acid substitutions.

Also included are polypeptide fragments that comprise less than the full length of the protein as shown in FIG. 4 (SEQ ID NO:2). Such fragments, may be, for example, at least 10, at least 15, at least 20 at least 30, at least 50, or at least 75 amino acids in length. Such polypeptide fragments may be used for example, as immunogens to raise antibodies that may be used in research and diagnostic applications.

The invention also includes proteins and polypeptide fragments that show specific degrees of sequence similarity with the sequence as shown in FIG. 4 (SEQ ID NO:2) and that have germacrene C synthase biological activity. Such similarity may be, for example, at least 70%, at least 80%, at least 85%, at least 90%, or at least 95% similarity as measured by standard analysis software (e.g., Blastp, as discussed herein, using default parameters).

Also included are isolated nucleic acids that encode the above proteins and fragments thereof. Such nucleic acids include a nucleic acid with the sequence as shown in FIG. 6 (SEQ ID NO:1) and degenerate versions of such a nucleic acid. Such nucleic acids may encode a polypeptide with germacrene C synthase biological activity.

Also encompassed within the invention are polynucleotides of at least 15 nucleotides in length (e.g., at least 17, at least 30, at least 50, or at least 100 nucleotides in length) of the sequence as shown in FIG. 6 (SEQ ID NO:1). Such polynucleotides may be used, for instance, as probes or primers as described herein. Probes may be labeled with, for instance, radioactive, fluorescent, or biotin-avidin labels and used for the detection of nucleic acids that show a certain degree of similarity to the probe sequence, thereby detecting nucleic acid sequences related to the germacrene C synthase gene of the invention.

The invention also includes nucleic acids and polynucleotide fragments (of at least 15, at least 17, at least 30, at least 50, or at least 100 nucleotides in length) that hybridize under defined conditions of stringency with the nucleic acid sequence as shown in FIG. 6 (SEQ ID NO:1). Such conditions for stringency may include, for example, prehybridization at 65° C. for 4 h, followed by hybridization at 65° C. overnight, followed by washing at 65° C. in 2×NaCl-NaH$_2$PO$_4$-EDTA buffer with 0.5% SDS for 20 min. Nucleic acids of the invention may also hybridize with the sequence as shown in FIG. 6 (SEQ ID NO:1) under less stringent wash conditions, for instance conditions of 60° C. and 0.5×SSC; 55° C. and 0.5×SSC; 50° C. and 2×SSC or even 45° C. to as low as room temperature and 2×SSC.

The invention also encompasses recombinant nucleic acids that include a nucleic acid (or polynucleotide) as described above. Such a recombinant nucleic acid may include a promoter sequence operably linked to a nucleic acid (or polynucleotide) of the invention such that a protein is expressed under appropriate conditions.

The invention also includes cells and organisms (e.g., plants) that contain such recombinant nucleic acids. Such plants may display enhanced pathogen (and/or herbivore) resistance and may also show altered flavor or odor.

According to another embodiment of the invention, methods are provided for expressing a germacrene C synthase polypeptide in a cell. Such methods including the steps of providing a cell that comprises a polynucleotide that includes a polypeptide-encoding sequence that encodes a polypeptide with germacrene C synthase biological activity and that has at least 70% amino acid sequence identity with a native germacrene C synthase polypeptide or a homolog thereof; and culturing the cell under conditions suitable for expression of the polypeptide.

According to another embodiment of the invention, methods are provided for producing a plant having an altered phenotype selected from the group consisting of altered flavor, altered odor, and increased defense against a pathogen or herbivore. The method comprises providing a plant comprising a polynucleotide as described above and growing the plant under conditions that cause expression of the polypeptide.

According to another embodiment of the invention, methods are provided for obtaining a germacrene C synthase gene or an allele or homolog thereof. Such methods comprise the steps of contacting a polynucleotide of an organism under stringent hybridization conditions with a probe or primer comprising a polynucleotide that includes at least 15 consecutive nucleotides of a germacrene C synthase gene of FIG. 6 (SEQ ID NO:1) that hybridizes specifically to the germacrene C synthase gene of FIG. 6 (SEQ ID NO:1) or an allele or homolog thereof. This causes the probe or primer to hybridize to a gene of the organism. The methods also include isolating the gene of the organism to which the probe or primer hybridizes.

The foregoing and other objects and advantages of the invention will become more apparent from the following detailed description and accompanying drawings.

SEQUENCE LISTING

SEQ ID NO:1 shows the nucleotide sequence of the cDNA insert of pLE20.3 (see FIG. 6).

SEQ ID NO:2 shows the amino acid sequence of the germacrene C synthase protein corresponding to the open reading frame of pLE20.3 (see FIGS. 4 and 7).

SEQ ID NO:3 shows the nucleotide sequence of the cDNA insert of pLE14.2 (see FIG. 8).

SEQ ID NO:4 shows the amino acid sequence corresponding to the open reading frame of the cDNA insert of pLE14.2 (see FIG. 9).

SEQ ID NO:5 shows the degenerate forward primer used to amplify 'VFNT Cherry' leaf library cDNA by PCR as described herein ("PCR-Based Probe Generation and cDNA Library Screening.")

SEQ ID NO:6 shows the degenerate reverse primer used to amplify 'VFNT Cherry' leaf library cDNA by PCR as described herein ("PCR-Based Probe Generation and cDNA Library Screening.")

BRIEF DESCRIPTION OF THE DRAWINGS

FIG. 4 shows the deduced amino acid sequence (SEQ ID NO:2) of the germacrene C synthase polypeptide encoded by the cDNA insert (SEQ ID NO:1) of pLE20.3 (GENBANK accession no. AF035630). Residues in bold are the conserved, aspartate-rich motif involved in binding the divalent metal ion-chelated substrate. Underlined residues indicate the region of the cDNA to which the probe was directed. Double-underlined residues are changed to S, S, T, and P, respectively, in the cDNA insert pLE14.2 (GENBANK accession no. AF035631).

FIG. 3 shows a proposed mechanism for the formation of germacrenes from FDP. OPP denotes the diphosphate moiety. δ-Elemene is not a direct enzyme product but is produced by thermal rearrangement of germacrene C.

FIG. 6 shows the nucleotide sequence of the cDNA insert of the cDNA clone pLE20.3 (SEQ ID NO:1). The ATG start codon (nt 39) and the TAA stop codon (nt 1683) are underlined.

FIG. 7 shows the deduced amino acid sequence of the open reading frame of pLE20.3 (SEQ ID NO:2).

FIG. 8 shows the nucleotide sequence of the cDNA insert of the cDNA clone pLE14.2 (SEQ ID NO:3). The start (ATG) and stop (TAA) codons corresponding to the open reading frame are underlined.

FIG. 9 shows the deduced amino acid sequence of the open reading frame of the cDNA clone pLE14.2 (SEQ ID NO:4).

DETAILED DESCRIPTION OF THE PREFERRED EMBODIMENTS

Figure 1:
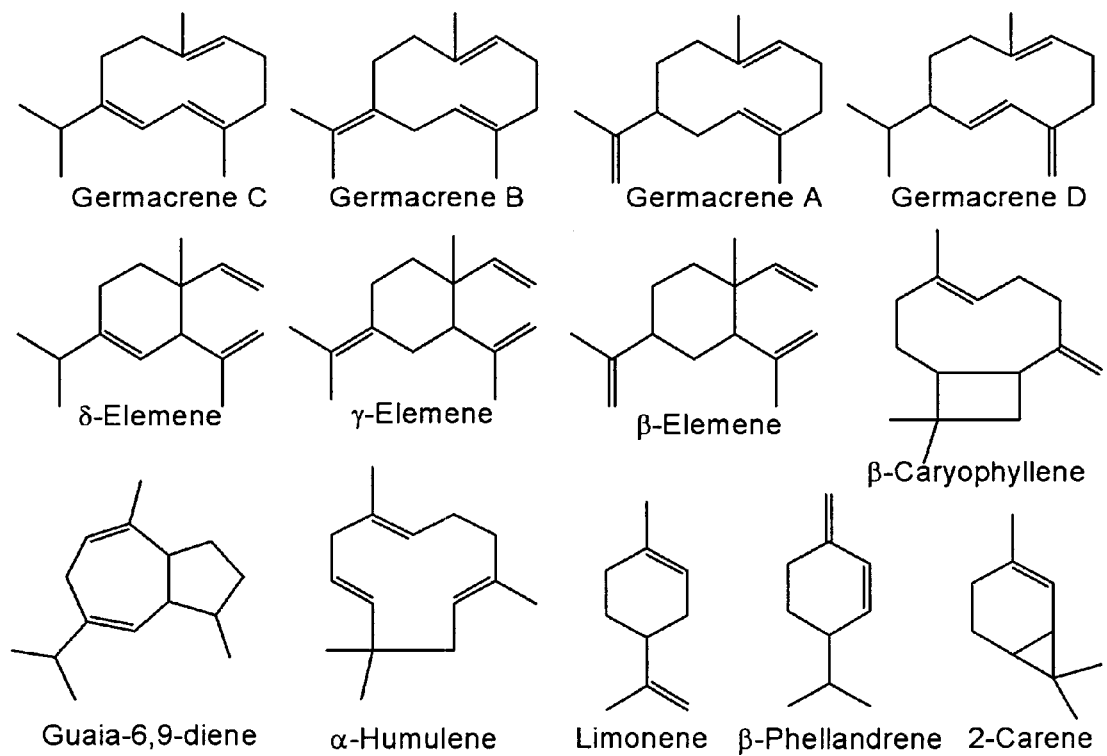
FIG. 1 shows sesquiterpene and monoterpene olefins of tomato essential oil. The elemenes formed by Cope rearrangement are shown beneath the corresponding germacrenes.

Discussed herein are the monoterpene and sesquiterpene composition of 'VFNT Cherry' tomato leaves, leaf sesquiterpene cyclase enzymology, the PCR strategy employed to isolate a cDNA encoding germacrene C synthase, and the comparison of this sesquiterpene cyclase to other plant terpenoid cyclases. 'VFNT Cherry' is a good model system for understanding the molecular basis of sesquiterpene biosynthesis and of glandular trichome-based expression of defense genes from which novel forms of resistance can be developed.

Germacrene C was found to be the most abundant sesquiterpene in the leaf oil of *Lycopersicon esculentum* cv. 'VFNT Cherry', with lesser amounts of germacrene A, guaia-6,9-diene, germacrene B, β-caryophyllene, α-humulene, and germacrene D. Soluble enzyme preparations from leaves catalyzed the divalent metal ion-dependent cyclization of [1-$^3$H]farnesyl diphosphate to these same sesquiterpene olefins, as determined by radio-GC.

To obtain a germacrene synthase cDNA, a set of degenerate primers was constructed, based on conserved amino acid sequences of related terpenoid cyclases. With cDNA prepared from leaf epidermis-enriched mRNA, these primers amplified a 767 base-pair (bp) fragment that was employed as a hybridization probe to screen the cDNA library. Thirty-one clones were evaluated for functional expression of terpenoid cyclase activity in *Escherichia coli* using labeled geranyl, farnesyl, and geranylgeranyl diphosphates as substrates. Nine cDNA isolates expressed sesquiterpene synthase activity, and GC-MS analysis of the products identified germacrene C with smaller amounts of germacrene A, B, and D. None of the expressed proteins was active with geranylgeranyl diphosphate; however, one truncated protein converted geranyl diphosphate to the monoterpene limonene. The cDNA inserts specify a deduced polypeptide of 548 amino acids (64,114 daltons), and sequence comparison with other plant sesquiterpene cyclases indicates that germacrene C synthase most closely resembles cotton δ-cadinene synthase (50% identity).

The germacrene C synthase genes disclosed herein makes possible the cloning of alleles and homologs of germacrene C synthase genes.

A germacrene C synthase allele or homolog or other genes having related sequences can be isolated from an organism by using primers or probes based on the germacrene C synthase gene sequences disclosed herein or using antibodies specific for germacrene C synthase(s), for example, according to conventional methods.

Knowledge of the germacrene C synthase gene sequences disclosed herein permits the modification of these sequences, as described more fully below, to produce variant forms of the genes and their polypeptide gene products.

The germacrene C synthase gene of the invention may be expressed transgenically in plants or in other organisms. For instance, the germacrene C synthase gene of the invention may be cloned into a vector (for instance, by using the *Agrobacterium tumefaciens* Ti vector) that facilitates the transfer of the gene into a plant genome. Transformation may be achieved, for example, by chemically induced transfer (e.g., with polyethylene glycol); biolistics; and microinjection. See, e.g., An et al., *Plant Molecular Biology Manual* A3:1–19, 1988. Once transferred, the gene may be expressed in the plant cell to induce enhanced resistance to pathogens and to make the plant less palatable to herbivores. Expression of the gene may be under the control of a host promoter or may be under the control of a non-host promoter operatively linked to the gene. Such non-host promoters commonly may include, for example, the CaMV 35S promoter (and related viral promoters), which may be used singly or in multimeric units to give various degrees of expression. Tetracycline (Tet)-based promoters may also be used in plants, as may various tissue-specific promoters which may be used to express germacrene C synthase in, for example, a root or shoot or flower, as appropriate. For example, the 2S seed storage protein and metallothionein-like promoter, wound-inducible promoter, infection-inducible promoter, Pin II promoter or vst1 promoter may be used. Such a promoter may be tissue- or organ-specific. For instance, leaf-specific promoters may be used to discourage leaf-eating herbivores. Fruit-specific promoters may be used alter flavor and/or deter fruitivores or fruit-destroying pests, e.g., fungi.

The germacrene C synthase gene of the invention may also be expressed in non-plant cells, such as bacterial, yeast, or insect cells. Expression systems for protein expression in such organisms are commercially available. Examples of such expression systems available from Invitrogen (Carlsbad, Calif.) include prokaryotic systems such as the pBAD system that allows tightly controlled expression and the pSE420 system that allows optimized translation of eukaryotic proteins; yeast systems such as the pYES system that facilitates episomal expression and a high vector copy-number and the classical Pichia system that facilitates high expression and copy number control; and insect expression systems such as the DES system that allows constitutive of inducible expression and the baculovirus system that allows high-level expression.

The invention includes a purified protein having a primary amino acid sequence as shown in FIG. 4 (SEQ ID NO:2). As well as proteins with a primary amino acid sequence that differs from the sequence as shown in FIG. 4 (SEQ ID NO:2) only by one or more conservative amino acid substitutions. Also included are polypeptide fragments that comprise less than the full length of the protein as shown in FIG. 4 (SEQ ID NO:2) and proteins that show specific degrees of sequence similarity with the sequence as shown in FIG. 4 (SEQ ID NO:2). Also included are isolated nucleic acids that encode the above proteins and polypeptides. Also encompassed within the invention are polynucleotides of at least 15 nucleotides in length that may be used, for instance, as probes or primers. The invention also includes nucleic acid fragments of at least 15 nucleotides in length that hybridize under defined conditions of stringency with the nucleic acid sequence as shown in FIG. 6 (SEQ ID NO:1). The invention also encompasses recombinant nucleic acids that include a polynucleotide as described above operably linked to a promoter, and cells and organisms (e.g., plants) that contain such recombinant nucleic acids. Such plants may display enhanced pathogen resistance and may also have altered flavor.

Methods for expressing a germacrene C synthase polypeptide in a cell and for producing a plant having an altered phenotype are also provided.

Methods for obtaining a germacrene C synthase gene or an allele or homolog thereof are, likewise, within the scope of the invention.

DEFINITIONS AND METHODS

The following definitions and methods are provided to better define the present invention and to guide those of ordinary skill in the art in the practice of the present invention. Definitions of common terms in molecular biology may also be found in Rieger et al., *Glossary of Genetics: Classical and Molecular*, 5th ed., Springer-Verlag, New York, 1991; and Lewin, *Genes V*, Oxford University Press, New York, 1994.

The term "plant" encompasses any plant and progeny thereof. The term also encompasses parts of plants, including seed, cuttings, tubers, fruit, flowers, etc.

A "reproductive unit" of a plant is any totipotent part or tissue of the plant from which one can obtain a progeny of the plant, including, for example, seeds, cuttings, buds, bulbs, somatic embryos, cultured cell (e.g., callus or suspension cultures), etc.

Nucleic Acids

Nucleic acids (a term used interchangeably with "polynucleotides" herein) that are useful in the practice of the present invention include the isolated germacrene C synthase genes, alleles of these genes, their homologs in other plant species, and fragments and variants thereof.

The term "germacrene C synthase gene" refers to any nucleic acid that contains a germacrene C synthase sequence having substantial similarity (at least 70% nucleic acid identity) to any of the germacrene C synthase genes from *Lycopersicon esculentum* shown in FIG. 6 (SEQ ID NO:1). Preferably such nucleic acids have germacrene C synthase enzymatic activity. This term relates primarily to the isolated full-length germacrene C synthase cDNA and the corresponding genomic sequences (including flanking or internal sequences operably linked thereto, including regulatory elements and/or intron sequences), and to fragments, alleles, homologs, and variants or modified forms thereof.

The term "native" refers to a naturally-occurring ("wild-type") nucleic acid or polypeptide.

A "homolog" of a germacrene C synthase gene is a gene sequence encoding a germacrene C synthase isolated from an organism other than *Lycopersicon esculentum*.

An "isolated" nucleic acid is one that has been substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

"Fragments", "probes" and "primers" are defined as follows. A fragment of a germacrene C synthase nucleic acid according to the present invention is a portion of the nucleic acid that is less than the full-length germacrene C synthase nucleic acid, and comprises at least a minimum length capable of hybridizing specifically with the germacrene C synthase nucleic acid of FIG. 6 (SEQ ID NO:1) under stringent hybridization conditions. The length of such a fragment is preferably 15–17 nucleotides (or base pairs) or more, more preferably at least 30 nucleotides, yet more preferably at least 50 nucleotides, and yet more preferably at least 100 nucleotides.

Nucleic acid probes and primers can be prepared based on the germacrene C synthase gene sequence provided in FIG. 6 (SEQ ID NO:1). A "probe" is an isolated DNA or RNA attached to a detectable label or reporter molecule, e.g., a radioactive isotope, ligand, chemiluminescent agent, or enzyme. "Primers" are isolated nucleic acids, generally DNA oligonucleotides 15 nucleotides or more in length, that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Methods for preparing and using probes and primers are described, for example, in Sambrook et al. (eds.), *Molecular Cloning: A Laboratory Manual,* 2nd ed., vol. 1–3, Cold Spring Harbor Laboratory Press, Cold Spring Harbor, NY, 1989; Ausubel et al. (eds.), *Current Protocols in Molecular Biology,* Greene Publishing and Wiley-Interscience, New York, 1987 (with periodic updates); and Innis et al., *PCR Protocols: A Guide to Methods and Applications,* Academic Press: San Diego, 1990. PCR-primer pairs can be derived from a known sequence, for example, by using computer programs intended for that purpose such as Primer (Version 0.5, ©1991, Whitehead Institute for Biomedical Research, Cambridge, Mass.).

Nucleotide "sequence similarity" is a measure of the degree to which two polynucleotide sequences have identical nucleotide bases at corresponding positions in their sequences when optimally aligned (with appropriate nucleotide insertions or deletions). Sequence similarity can be determined using sequence analysis software (set at default parameters) such as the Sequence Analysis Software Package of the Genetics Computer Group (University of Wisconsin Biotechnology Center, Madison, Wis.) or the Basic Local Alignment Tool (BLAST) available from the National Center for Biotechnology Information (BLAST) (www.ncbi.nlm.nih.gov/BLAST). For example, the BLASTn program can be used with default parameters to determine nucleotide sequence similarity between two nucleotides.

A variant form of a germacrene C synthase polynucleotide may have at least 70%, at least 80%, at least 90%, or at least 95% nucleotide sequence similarity with a native germacrene C synthase gene as shown in FIG. 6 (SEQ ID NO:1).

A first nucleic-acid sequence is "operably linked" with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

A "recombinant" nucleic acid is an isolated polypeptide made by an artificial combination of two otherwise separated segments of sequence, e.g., by chemical synthesis or by the manipulation of isolated segments of nucleic acids by genetic engineering techniques.

The production of a recombinant nucleic acid of the invention may involve the ligation of a promoter sequence to a nucleic acid of the invention such that the two elements are operably linked and protein is expressed under appropriate conditions in vitro or in vivo. Techniques for nucleic-acid manipulation are described generally in, for example, Sambrook et al. (1989) and Ausubel et al. (1987, with periodic updates). Vectors suitable for the production of intact native proteins include pKC30 (Shimatake and Rosenberg, *Nature* (London) 292:128, 1981), pKK177-3 (Amann and Brosius, *Gene* 40:183, 1985), and pET-3 (Studiar and Moffatt, *J. Mol. Biol.* 189:113, 1986). Expression systems are commercially available, for instance, the Pichia yeast expression systems provided by Invitrogen. Methods for chemical synthesis of nucleic acids are discussed, for example, in Beaucage and Carruthers, *Tetra. Letts.* 22:1859–1862, 1981; and Matteucci et al., *J. Am. Chem. Soc.* 103:3185, 1981. Chemical synthesis of nucleic acids can be performed, for example, on commercial automated oligonucleotide synthesizers.

Preparation of Recombinant or Chemically Synthesized Nucleic Acids; Vectors, Transformation, Host Cells Natural or synthetic nucleic acids according to the present invention can be incorporated into recombinant nucleic-acid constructs, typically DNA constructs, capable of introduction into and replication in a host cell. Such a construct preferably is a vector that includes a replication system and sequences that are capable of transcription and translation of a polypeptide-encoding sequence in a given host cell. For the practice of the present invention, conventional compositions and methods for preparing and using vectors and host cells are employed, as discussed, inter alia, in Sambrook et al., 1989, or Ausubel et al., 1987.

A "transformed" or "transgenic" cell, tissue, organ, or organism is one into which a foreign nucleic acid, has been introduced. A "transgenic" or "transformed" cell or organism also includes (1) progeny of the cell or organism and (2) progeny produced from a breeding program employing a "transgenic" plant as a parent in a cross and exhibiting an altered phenotype resulting from the presence of the "transgene," i.e., the recombinant germacrene C synthase nucleic acid. In the case of germacrene C synthase, transgenic expression in a plant confers increased host defense against pathogens, including but not limited to microbial and fungal pathogens, and pests, including but not limited to herbivores such as arthropod or mammalian herbivores. Also, expression of germacrene C synthase can change the aroma and/or flavor profile of a plant or plant part, such as flowers, fruits, vegetables berries, leaves, etc. Where desirable, tissue- or organ-specific promoters can be used to increase germacrene C synthase expression in specific tissues in which increased expression is desired for these purposes, e.g., leaf- or trichome-specific promoters to discourage herbivory or fruit or flower-specific promoters to alter aroma or flavor profiles. Any plant (angiosperms, gymnosperms, etc.) would be a suitable candidate for transgenic expression, since all plants make the precursors for the germacrene C synthase enzyme.

Nucleic-Acid Hybridization; "Stringent Conditions"; "Specific"

The nucleic-acid probes and primers of the present invention hybridize under stringent conditions to a target DNA sequence, e.g., to a germacrene C synthase gene.

The term "stringent conditions" is functionally defined with regard to the hybridization of a nucleic-acid probe to a target nucleic acid (i.e., to a particular nucleic-acid sequence of interest) by the hybridization procedure discussed in Sambrook et al., 1989, at 9.52–9.55. See also, Sambrook et al., 1989, at 9.47–9.52, 9.56–9.58; Kanehisa, *Nucl. Acids Res.* 12:203–213, 1984; and Wetmur and Davidson, *J. Mol. Biol.* 31:349–370, 1968. In general, wash conditions should include a wash temperature that is approximately 12–20° C. below the calculated $T_m$ (melting temperature) of the hybrid pair under study (Sambrook et al., 1989, pp. 9–51). Melting temperature for a hybrid pair may be calculated by the following equation:

$$T_m = 81.5° C. - 16.6 (\log_{10}[Na^+]) + 0.41 (\% G+C) - 0.63 (\% \text{formamide}) - (600/L)$$

where L=the length of the hybrid in base pairs.

Typical conditions for hybridization between a polynucleotide of the invention and the nucleotide sequence as shown in FIG. 6 (SEQ ID NO:1) are, for instance, prehybridization at 65° C. for 4 h, followed by hybridization at 65° C. overnight, followed by washing at 65° C. in 2×NaCl-NaH$_2$PO$_4$-EDTA buffer with 0.5% SDS for 20 min.

The inventors have determined "generic" conditions used during experimentation described herein. These conditions are set out below:

| Very High Stringency (sequences 90% identical or greater) | | |
|---|---|---|
| Hybridization in 5x SSC at | 65° C. | 16 h |
| Wash twice in 2x SSC at | room temp. | 15 min each |
| Wash twice in 0.2x SSC at | 65° C. | 20 min each |
| High Stringency (sequences 80% identical or greater) | | |
| Hybridization in 3x SSC at | 65° C. | 16 h |
| Wash twice in 2x SSC at | room temp. | 20 min each |
| Wash once in 0.5x SSC at | 55° C. | 20 min |
| Low Stringency (sequences down to −50% identity) | | |
| Hybridization in 3x SSC at | 65° C. | 16 h |
| Wash twice in 2x SSC at | 45° C. to as low as room temp. | 20 min each |

Regarding the amplification of a target nucleic-acid sequence (e.g., by PCR) using a particular amplification primer pair, stringent conditions are conditions that permit the primer pair to hybridize only to the target nucleic-acid sequence to which a primer having the corresponding wild-type sequence (or its complement) would bind and preferably to produce a unique amplification product.

The term "specific for (a target sequence)" indicates that a probe or primer hybridizes under stringent conditions only to the target sequence in a sample comprising the target sequence.

Nucleic-Acid Amplification

As used herein, "amplified DNA" refers to the product of nucleic-acid amplification of a target nucleic-acid sequence. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202, and in Innis et al. (eds.), *PCR Protocols: A Guide to Methods and Applications*, Academic Press, San Diego, 1990.

Methods of Obtaining cDNA Clones Encoding Alleles, Homologs, and Related Gene Sequences Other germacrene C synthase genes (e.g., alleles and homologs of the germacrene C synthases disclosed herein) can be readily obtained from a wide variety of species by cloning methods known in the art using probes and primers based on the germacrene C synthase genes described herein.

One or more primer pairs based on a germacrene C synthase sequence can be used to amplify such alleles, homologs, or related genes by the polymerase chain reaction (PCR) or other conventional amplification methods. Alternatively, the disclosed germacrene C synthase cDNAs or fragments thereof or antibodies specific for germacrene C synthase can be used to probe a cDNA or genomic library by conventional methods.

Cloning of Germacrene C Synthase Genomic Sequences

Genomic clones corresponding to a germacrene C synthase cDNA (including the promoter and other regulatory regions and intron sequences) can be obtained by conventional methods from a genomic library or by amplification of genomic DNA by conventional methods using one or more germacrene C synthase probes or primers (i.e., individually or as a pooled probe).

Germacrene C synthase genes can be obtained by hybridization of a germacrene C synthase probe to a cDNA or genomic library of a target species. Such a homolog can also be obtained by PCR or other amplification method from genomic DNA or RNA of a target species using primers based on the germacrene C synthase sequence shown in FIG.

6 (SEQ ID NO:1). Genomic and cDNA libraries from tomato or other plant species can be prepared by conventional methods.

Primers and probes based on the sequence shown in FIG. 6 (SEQ ID NO:1) can be used to confirm (and, if necessary, to correct) the germacrene C synthase sequences disclosed herein by conventional methods.

Nucleotide-Sequence Variants of a Germacrene C Synthase cDNA and Amino Acid Sequence Variants of a Germacrene C Synthase Protein Using the nucleotide and the amino-acid sequences of the germacrene C synthases disclosed herein, those skilled in the art can create DNA molecules and polypeptides that have minor variations in their nucleotide or amino acid sequence.

"Variant" DNA molecules are DNA molecules containing minor changes in a native germacrene C synthase sequence, i.e., changes in which one or more nucleotides of a native germacrene C synthase sequence is deleted, added, and/or substituted, preferably while substantially maintaining germacrene C synthase activity. Variant DNA molecules can be produced, for example, by standard DNA-mutagenesis techniques or by chemically synthesizing the variant DNA molecule or a portion thereof. Such variants preferably do not change the reading frame of the protein-coding region of the nucleic acid and preferably encode a protein having no change, only a minor reduction, or an increase in germacrene C synthase biological function.

Amino-acid substitutions are preferably substitutions of single amino-acid residues. DNA insertions are preferably of about 1 to 10 contiguous nucleotides and deletions are preferably of about 1 to 30 contiguous nucleotides. Insertions and deletions are preferably insertions or deletions from an end of the protein-coding or non-coding sequence and are preferably made in adjacent base pairs. Substitutions, deletions, insertions, or any combination thereof can be combined to arrive at a final construct.

Preferably, variant nucleic acids according to the present invention are "silent" or "conservative" variants. "Silent" variants are variants of a given nucleic acid sequence in which there has been a substitution of one or more base pairs but no change in the amino-acid sequence of the polypeptide encoded by the sequence. "Conservative" variants are variants of a given nucleic acid sequence in which at least one codon in the protein-coding region of the gene has been changed, resulting in a conservative change in one or more amino acid residues of the polypeptide encoded by the nucleic-acid sequence, i.e., an amino acid substitution.

A number of examples of conservative amino acid substitutions are listed below. In addition, one or more codons encoding cysteine residues can be substituted for, resulting in a loss of a cysteine residue and affecting disulfide linkages encoded polypeptide.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Alu | Asp |
| Gly | Pro |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function are made by selecting substitutions that are less conservative than those listed above, e.g., causing changes in: (a) the structure of the polypeptide backbone in the area of the substitution; (b) the charge or hydrophobicity of the polypeptide at the target site; or (c) the bulk of an amino acid side chain. Substitutions generally expected to produce the greatest changes in protein properties are those in which: (a) a hydrophilic residue; e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

A germacrene C synthase gene sequence can be modified, for example, as follows:

(1) To improve expression efficiency:

One or more codons can be changed to conform the gene to the codon-usage bias of the host cell for improved expression. Enzymatic stability can be altered by removing or adding one or more cysteine residues, thus removing or adding one or more disulfide bonds. Hetrologous expression efficiency may be improved by use of vectors such as pSBET (that encodes a tRNA for two rare arginine codons) (Williams et al., *Biochemistry* 37(35):12213–12220, 1998). Increased expression may be had by using the vector pT-GroE (that encodes chaperone GroELS) (Tanaka et al, *Biochim. Biophys. Acta* 1343(2):335–348, 1997). Improved folding and catalytic efficiency of recombinant synthase may be obtained by using the vector pT-Trx that encodes a thioredoxin-fusion protein that enhances solubility.

(2) To alter catalytic efficiency:

One or more conserved or semi-conserved residues, including those located at the active site of a germacrene C synthase, can be mutagenized to alter enzyme kinetics.

As noted below, germacrene C synthase includes the aspartate-rich motif DDXXD found in most prenyltransferases and terpenoid cyclases and thought to play a role in substrate/intermediate binding. By increasing the aspartate content of the DDXXD motif (where D is aspartate and X is any amino acid), it is possible to increase the enzymatic rate (i.e., the rate-limiting ionization step of the enzymatic reaction). Arginines have been implicated in binding or catalysis, and conserved arginine residues are also good targets for mutagenesis. Changing the conserved DDXXD motif (e.g., the aspartate residues thereof) by conventional site-directed mutagenesis methods to match those of other known enzymes can also lead to changes in the kinetics or substrate-specificity of germacrene C synthase.

(3) To modify substrate utilization and/or products:

The enzyme, particularly the active site, can be modified to allow the enzyme to bind shorter or longer carbon chains than the unmodified enzyme. Substrate-size utilization can be altered by increasing or decreasing the size of the hydrophobic patches to modify the size of the hydrophobic pocket of the enzyme. For instance, the clone pLE11.3 (discussed herein under "Sequence Analysis") contains a truncated version of the germacrene C synthase gene, and expresses a monoterpene (limonene) synthase enzyme that uses geranyl diphosphate ($C_{10}$) as a substrate. This shows that catalytic flexibility can be engineered into germacrene C synthase by modification of the N-terminus (see below). Domain swapping can also be used to alter substrate preferences, products, or other biochemical or physical properties of the germacrene C synthase polypeptide. Domain swapping can be accomplished by replacing a portion of a native germacrene C synthase protein-coding sequence with a corresponding portion of a candidate protein-coding sequence (e.g., switching all or part of the active site) so as to preserve the correct reading frame, using standard recombinant DNA techniques (e.g., by PCR). Candidate sequences for domain swapping include, but are not limited to, the following: various sesquiterpene synthases, including epi-aristolochene synthase (Facchini and Chappell, *Proc. Nat. Acad. Sci. USA* 89:11088, 1992); vetispiradiene synthase (Back and Chappell, *J. Biol. Chem.* 270:7375, 1995); farnesene synthase (Crock et al., *Proc. Nat. Acad. Sci. USA* 94:12833, 1997); cadinene synthase (Chen et al., *Arch. Biochem. Biophys.* 324:255, 1995); δ-selinene synthase and γ-humulene synthase (Steele et al., *J. Biol. Chem.* 273:2078, 1998); and bisabolene synthase (Croteau et al., unpublished); various monoterpene synthases, including limonene synthase (Colby et al., *J. Biol. Chem.* 268:23016, 1993); myrcene synthase, limonene synthase, and pinene synthase (Bohlmann et al., *J. Biol. Chem.* 272:21784, 1997); 1,8-cineole synthase, bornyl diphosphate synthase, and sabinene synthase (Croteau, unpublished); and linalool synthase (Dudareva et al., *Plant Cell* 8:1137, 1996).

(4) To change product outcome:

Directed mutagenesis of conserved residues, particularly at the active site, can be used to permit the enzyme to produce different products. See, e.g., Cane et al., *Biochemistry* 34:2480–2488, 1995; Joly and Edwards, *J. Biol. Chem.* 268:26983–26989, 1993; Marrero et al., *J. Biol. Chem.* 267:533–536, 1992; and Song and Poulter, *Proc. Natl. Acad. Sci. USA* 91:3044–3048, 1994). The product of the clone pLE11.3 (discussed herein) is an example of such mutagenesis that leads to production of a different product (limonene).

Expression of Germacrene C Synthase Polynucleotides in Host Cells

DNA constructs incorporating a germacrene C synthase gene or fragment thereof according to the present invention preferably place the germacrene C synthase protein coding sequence under the control of an operably linked promoter that is capable of expression in a host cell.

Various promoters suitable for expression of heterologous genes in plant cells are known in the art, including constitutive promoters, e.g., the cauliflower mosaic virus (CaMV) 35S promoter and other constitutive promoters, which is expressed in many plant tissues, organ- or tissue-specific promoters, wound-inducible promoters, and promoters that are inducible by chemicals such as methyl jasmonate, salicylic acid, or safeners, for example. A variety of other well-known promoters or other sequences useful in constructing expression vectors are available for expression in bacterial, yeast, mammalian, insect, amphibian, avian, or other host cells.

Polypeptides

The term "germacrene C synthase protein" (or polypeptide) refers to a protein encoded by a germacrene C synthase gene, including alleles, homologs, and variants thereof. Also encompassed are fragments and modified forms of such polypeptides as defined below.

A germacrene C synthase polypeptide can be produced by the expression of a recombinant germacrene C synthase nucleic acid or be chemically synthesized. Techniques for chemical synthesis of polypeptides are described, for example, in Merrifield, *J. Amer. Chem. Soc.* 85:2149–2156, 1963.

Polypeptide Sequence Identity and Similarity

Amino acid sequence "identity" (or "homology") is a measure of the degree to which aligned amino acid sequences possess identical amino acids at corresponding positions. Amino acid sequence "similarity" is a measure of the degree to which aligned amino acid sequences possess identical amino acids or conservative amino acid substitutions at corresponding positions. Sequence identity and similarity can be determined using sequence-analysis software (set at default parameters) such as the Sequence Analysis Software Package of the Genetics Computer Group (University of Wisconsin Biotechnology Center, Madison, Wis.) or the Basic Local Alignment Tool (BLAST) available from the National Center for Biotechnology Information (BLAST) (www.ncbi.nlm.nih.gov/BLAST). For example, the BLASTp program can be used with default parameters to determine amino acid sequence similarity between two proteins.

Ordinarily, germacrene C synthase polypeptides encompassed by the present invention have at least about 70% amino acid sequence "identity" (or homology) compared with a native germacrene C synthase polypeptide, preferably at least about 80% identity, more preferably at least about 85% identity, yet more preferably at least about 90% identity, and yet more preferably at least about 95% identity to a native germacrene C synthase polypeptide. Preferably, such polypeptides also possess characteristic structural features and biological activity of a native germacrene C synthase polypeptide.

A germacrene C synthase "biological activity" includes germacrene C synthase enzymatic activity as determined by conventional methods (e.g., as described in the Example below). Other biological activities of germacrene C synthase include, but are not limited to, substrate binding, immunological activity (including the capacity to elicit the production of antibodies that are specific for germacrene C synthase), etc.

"Isolated," "Purified," "Homogeneous" Polypeptides

A polypeptide is "isolated" if it has been separated from the cellular components (nucleic acids, liquids, carbohydrates, and other polypeptides) that naturally accompany it. Such a polypeptide can also be referred to as "pure" or "homogeneous" or "substantially" pure or homogeneous. Thus, a polypeptide which is chemically synthesized or recombinant (i.e., the product of the expression of a recombinant nucleic acid, even if expressed in a homologous cell type) is considered to be isolate. A monomeric polypeptide is isolated when at least 60–90% by weight of a sample is composed of the polypeptide, preferably 95% or more, and more preferably more than 99%. Protein purity or homogeneity is indicated, for example, by polyacrylamide gel electrophoresis of a protein sample, followed by visualization of a single polypeptide band upon staining the polyacrylamide gel; high-performance liquid chromatography; or other conventional methods.

Protein Purification The polypeptides of the present invention can be purified by any of the means known in the art. Various methods of protein purification are described, e.g., in *Guide to Protein Purification*, in Deutscher (ed.), *Meth. Enzymol.* 185, Academic Press, San Diego, 1990; and Scopes, *Protein Purification: Principles and Practice*, Springer Verlag, New York, 1982.

Variant Forms of Germacrene C Synthase Polypeptides; Labeling

Encompassed by the germacrene C synthase polypeptides according to an embodiment of the present invention are variant polypeptides in which there have been substitutions, deletions, insertions, or other modifications of a native germacrene C synthase polypeptide. The variants substantially retain structural and/or biological characteristics and are preferably silent or conservative substitutions of one or a small number of contiguous amino acid residues. Preferably, such variant polypeptides are at least 70%, more preferably at least 80%, and most preferably at least 90% homologous to a native germacrene C synthase polypeptide.

The native germacrene C synthase polypeptide sequence can be modified by conventional methods, e.g., by acetylation, carboxylation, phosphorylation, glycosylation, ubiquitination, and labeling, whether accomplished by in vivo or in vitro enzymatic treatment of a germacrene C synthase polypeptide or by the synthesis of a germacrene C synthase polypeptide using modified amino acids.

There are a variety of conventional methods and reagents for labeling polypeptides and fragments thereof. Typical labels include radioactive isotopes, ligands, or ligand receptors, fluorophores, chemiluminescent agents, and enzymes. Methods for labeling and guidance in the choice of labels appropriate for various purposes are discussed, e.g., in Sambrook et al. (1989) and Ausubel et al. (1987, with periodic updates).

Polypeptide Fragments

The present invention also encompasses fragments of germacrene C synthase polypeptides that lack at least one residue of a native full-length germacrene C synthase polypeptide yet retain at least one of the biological activities characteristic of germacrene C synthase, e.g., germacrene C synthase enzymatic activity or possession of a characteristic immunological determinant. As an additional example, an immunologically active fragment of a germacrene C synthase polypeptide is capable of raising germacrene C synthase-specific antibodies in a target immune system (e.g., murine or rabbit) or of competing with germacrene C synthase for binding to germacrene C synthase-specific antibodies, and is thus useful in immunoassays for the presence of germacrene C synthase polypeptides in a biological sample. Such immunologically active fragments typically have a minimum size of at least 7 to 17 amino acids. Fragments may comprise, for example at least 10, at least 20, or at least 30 consecutive amino acids of a native germacrene C synthase polypeptide.

Fusion Polypeptides

The present invention also provides fusion polypeptides including, for example, heterologous fusion polypeptides, i.e., a germacrene C synthase polypeptide sequence or fragment thereof and a heterologous polypeptide sequence, e.g., a sequence from a different polypeptide. Such heterologous fusion polypeptides thus exhibit biological properties (such as ligand-binding, catalysis, secretion signals, antigenic determinants, etc.) derived from each of the fused sequences. Fusion partners include, for example, immunoglobulins, beta galactosidase, trpE, protein A, beta lactamase, alpha amylase, alcohol dehydrogenase, yeast alpha mating factor, and various signal and leader sequences which, e.g., can direct the secretion of the polypeptide. Fusion polypeptides can also be produced by domain swapping, as described above. Fusion polypeptides are typically made by the expression of recombinant nucleic acids or by chemical synthesis.

Polypeptide Sequence Determination

The sequence of a polypeptide of the present invention can be determined by various methods known in the art. In order to determine the sequence of a polypeptide, the polypeptide is typically fragmented, the fragments separated, and the sequence of each fragment determined. To obtain fragments of a germacrene C Synthase polypeptide, the polypeptide can be digested with an enzyme such as trypsin, clostripain, or Staphylococcus protease, or with chemical agents such as cyanogen bromide, o-iodosobenzoate, hydroxylamine, or 2-nitro-5-thiocyanobenzoate. Peptide fragments can be separated, e.g., by reversed-phase high-performance liquid chromatography (HPLC) and analyzed by gas-phase sequencing.

Antibodies

The present invention also encompasses polyclonal and/or monoclonal antibodies that are specific for a germacrene C synthase, i.e., bind to a germacrene C synthase and are capable of distinguishing the germacrene C synthase polypeptide from other polypeptides under standard conditions. Such antibodies are produced and assayed by conventional methods.

For the preparation and use of antibodies according to the present invention, including various immunoassay techniques and applications, see, e.g., Goding, *Monoclonal Antibodies: Principles and Practice*, 2d ed., Academic Press, New York, 1986; and Harlow and Lane, *Antibodies: A Laboratory Manual*, Cold Spring Harbor Laboratory, Cold Spring Harbor, N.Y. 1988. Germacrene C synthase-specific antibodies are useful, for example, in: purifying germacrene C synthase polypeptides; cloning germacrene C synthase alleles and homologs from an expression library; and antibody probes for protein blots and immunoassays; etc.

Germacrene C synthase polypeptides and antibodies can be labeled by conventional techniques. Suitable labels include radionuclides, enzymes, substrates, cofactors, inhibitors, fluorescent agents, chemiluminescent agents, magnetic particles, etc.

Plant Transformation and Regeneration

Any well-known method can be employed for plant cell transformation, culture, and regeneration can be employed in the practice of the present invention. Methods for introduction of foreign DNA into plant cells include, but are not limited to: transfer involving the use of *Agrobacterium tumefaciens* and appropriate Ti vectors, including binary vectors; chemically induced transfer (e.g., with polyethylene glycol); biolistics; and microinjection. See, e.g., an et al., *Plant Molecular Biology Manual* A3:1–19, 1988.

The invention will be better understood by reference to the following Examples, which are intended to merely illustrate the best mode now known for practicing the invention. The scope of the invention is not to be considered limited thereto, however.

EXAMPLES

Materials and Methods

Experimental Materials

*L. esculentum cv.* 'VFNT Cherry' tomato plants (obtained as seed from John Steffens, Cornell University) were propagated from cuttings and grown under conditions previously reported (Crock et al., *Proc. Natl. Acad. Sci. USA* 94:12833–12838, 1997). *L. esculentum cv.* 'Better Boy' plants were obtained from C. A. Ryan(Washington State University) and similarly propagated. Methods have been previously reported for the preparation of [1-$^3$H]geranyl diphosphate (GDP) (122 Ci/mol) (Croteau et al., *Arch. Biochem. Biophys.* 309:184–192, 1994), [1-$^3$H]FDP (125 Ci/mol) (Dixit et al., *J. Org. Chem.* 46:1967–1969, 1981), and [1-$^3$H]geranylgeranyl diphosphate (GGDP) (90 Ci/mol) (LaFever et al., *Arch. Biochem. Biophys.* 313:139–149, 1994). Terpenoid standards were from the inventors' own collection or gifts from Bob Adams (Baylor University) or Larry Cool (University of California, Berkeley). The 'VFNT Cherry' tomato cDNA library, derived from epidermis-enriched, young leaf tissue, was also a gift from John Steffens. All other biochemicals were purchased from Sigma Chemical Co. or Aldrich Chemical Co., unless otherwise noted.

Volatile Terpene Analysis

Expanding tomato leaves were harvested, frozen in liquid $N_2$, and then subjected to simultaneous steam distillation-solvent (pentane) extraction (Maarse et al., *J. Agric. Food Chem.* 18:1095–1101, 1970) using the J&W Scientific apparatus. The resulting pentane phase, collected at 0–4° C., was passed over a column of $MgSO_4$-silica gel (Mallinckrodt SilicAR-60) to remove water and oxygenated compounds and provide the hydrocarbon fraction. To examine the possibility of thermal decomposition during distillation, leaf material was extracted directly with cold (−20° C.) pentane and the extract purified as before. To provide germacrene C for NMR studies, the distillate was separated by preparative TLC (20 cm×20 cm×1 mm, silica gel G containing 8% $AgNO_3$; plates dried, pre-run in diethyl ether and dried again, all steps in the dark) using benzene: hexane: acetonitrile (60:40:5, v/v/v) as developing solvent in the dark, with humulene, caryophyllene, and longifolene as standards. Bands were visualized under UV light after spraying with 0.2% dichlorofluorescein, and the triene region ($R_f$~0.3) was separated into 5 mm strips of gel from which the material was eluted with diethyl ether. Those fractions containing germacrene by GC analysis were concentrated under vacuum and dissolved in a minimum volume of acetonitrile, then emulsified with one-third volume of $H_2O$. The emulsion was injected onto an Alltech C-18 5U reversed phase column (4.6 mm i.d.×250 mm) installed on a Spectra-Physics SP8800 high-performance liquid chromatograph and eluted isocratically with acetonitrile: water (75:25, v/v) at a flow rate of 1.0 mL/min while monitoring at 220 nm. NaCl was added to fractions containing germacrene C before extraction with pentane, and the extract was passed through a column of $MgSO_4$-silica gel before determination of purity by GC.

Terpene Synthase Isolation and Assay

Immature folded leaves (ca. 15 g) from 'VFNT Cherry' were frozen in liquid $N_2$, ground to a fine powder and transferred to a centrifuge tube containing 15 mL of buffer (20 mM 3-(N-morpholino)-2-hydroxypropanesulfonic acid (pH 7.0), 20 mM β-mercaptoethanol, 10 mM sodium ascorbate, 1 mM EDTA, 10% (v/v) glycerol, 0.1% (w/v) $Na_2S_2O_5$, 1.0% (w/v) polyvinylpyrrolidone ($M_f$=ca. 40,000), 1.0% (w/v) polyvinylpolypyrrolidone, and 10 g Amberlite XAD-4 polystyrene resin beads). The tube was flushed with $N_2$, sealed and vigorously agitated, then centrifuged at 3200× g for 15 min at 4° C. A 2-mL portion of the supernatant was transferred to a glass, Teflon-sealed; screw-capped tube, and the contents adjusted to 1 mM $MnCl_2$, 10 mM $MgCl_2$ and 7.3 μM [1-$^3$H]FDP, then overlaid with 1 mL pentane before closure and incubation at 30° C. for 2 h. At the completion of the assay, the reaction mixture was extracted with pentane (2×1 mL), and the combined extract was passed through a $MgSO_4$-silica gel column to provide the terpene hydrocarbon fraction. The incubation mixture was next extracted with diethyl ether (2×1 mL), and the combined ether extract was passed through the corresponding column to provide the oxygenated terpenoids. An aliquot of each fraction was taken for liquid scintillation counting to determine conversion rate, and the remainder was concentrated under vacuum for capillary GC or radio-GC analysis. For radio-GC analysis, authentic carrier standards were added prior to solvent concentration to minimize losses. Boiled controls and incubations without divalent metal ion cofactors were included in all experiments.

PCR-Based Probe Generation and cDNA Library Screening

Comparison of the deduced amino acid sequences of a monoterpene cyclase [spearmint limonene synthase (Colby et al., *J. Biol. Chem.* 268:23016–23024, 1993)], a sesquiterpene cyclase [tobacco 5-epi-aristolochene synthase (TEAS; Facchini and Chappell, *Proc. Natl. Acad. Sci. USA* 89:11088–11092, 1992) ], and a diterpene cyclase [castor bean casbene synthase (Mau and West, *Proc. Natl. Acad. Sci. USA* 91:8497–8501, 1994) ] allowed the design of two degenerate oligonucleotide primers for PCR amplification based on conserved domains. The forward and reverse primers.

[5'-G(A)AIGGIA(G)AA(G)TTT(C)-AAA)G(GA-3' and

5'-T(C)TG(T)CATA(G)TAA(G)TCIGG(A)LAG-3']

were used to amplify 'VFNT Cherry' leaf library cDNA by PCR performed with the GeneAmp$^R$ PCR Reagent kit (Perkin Elmer Cetus) using 0.5 μcDNA template and 50 pmol of each primer per 50 μL reaction. (I=inosine) Following a hot start at 100° C. for 5 min, Taq DNA polymerase was added, and the reactions were cycled twice at 97° C. (1 min), 55° C. (1 min), and 72° C (2 min), then twice at 94° C. (1 min), 53° C. (1min), and 72° C. (2 min). While holding denaturing and extension temperatures constant, the annealing temperature was lowered by 2° C. each two cycles to 45° C., with a final extension at 75° C. for 5 min. PCR products were electrophoresed on a tris-(hydroxymethyl) aminomethane-$Na_2B_4O_7$-EDTA-2% agarose gel. Amplicons of the expected size (ca. 770 bp) were isolated by electrophoretic transfer to NA 45 paper (Schleicher & Schuell). The fragments were reamplified and repurified as above, then ligated into pCR-Script SK(+) using the Stratagene protocol and transformed into *E. coli* XL-1 Blue (Stratagene) by standard methods (Sambrook et al., 1989).

For Southern blot analysis, 10 μg each of isolated genomic DNA (Sambrook et al., 1989) from 'VFNT Cherry' leaf and spearmint leaf (as control) were digested with EcoRI, HindIII and BamHI restriction enzymes, electrophoresed on tris-(hydroxymethyl)aminomethane-$Na_2B_4O_7$-EDTA-0.8% agarose, and transferred to a Magna membrane (Micron Separations). The amplicon from above was excised using BamHI and NotI, and 40 ng were radiolabeled with [α-$^{32}$P]dATP (Random-Primed Labeling Kit, U.S. Biochemical Corp.), purified over Sephadex G-50, then added to 20 mL of hybridization buffer containing 6× NaCl-$NaH_2PO_4$-EDTA, 5× Denhardts, 0.5% SDS, 50 μg/mL denatured salmon sperm DNA, and 10% dextran sulfate. Prehybridization at 65° C. (4 h) was followed by hybridization at 65° C. overnight. The stringency wash was performed at 65°

C. in 2× NaCl-NaH$_2$PO$_4$-EDTA buffer with 0.5% SDS (20 min). Blots were exposed to Kodak XAR-5 film for 12 h at −70° C.

For cDNA library screening, the purified NotI/BamHI-digested amplicon from above was radiolabeled with $^{32}$P as before and used to screen 7.5×10$^5$ cDNA clones (plated at 2.5×10$^4$ pfu/150 mm plate) from a 'VFNT Cherry' leafλ cDNA library. Hybridization was conducted on nitrocellulose membranes (Schleicher & Schuell) in hybridization buffer without Denhardts at 65° C. (16 h). Blots were washed twice (5 min) in 6× NaCl-Na citrate-EDTA buffer at 20° C., then once (20 min) in 6× NaCl-Na citrate-EDTA buffer with 1% SDS at 37° C., and twice (30 min) at 65° C. Filters were exposed to Kodak XAR-5 film as above. Thirty-one positive plaques were purified through four additional cycles of hybridization, excised in vivo as Bluescript II (Stratgegene) phagemids and used to infect *E. coli* XL1-Blue from which plasmids were prepared using a purification column (Qiagen).

The clones were digested with RsaI, and the fragments were electrophoresed to sort into groups; insert size was determined by PCR using T3 and T7 promoter primers. DNA sequencing (both strands) was performed by Retrogen, San Diego, Calif., or by automated "DyeDeoxy Terminator Cycle Sequencing" (Applied Biosystems 373 Sequencer). DNA sequence analysis employed programs from the Genetics Computer Group (University of Wisconsin Package, version 8.0.1-Unix), and searches were done at the National Center for Biotechnology Information using the BLAST network service to search standard databases.

Expression of Terpenoid Synthase Activity

To evaluate functional expression of putative terpenoid synthases, *E. coli* XL1-Blue cells harboring the selected phagemid were grown, induced, harvested, and extracted (Crock et al., *Proc. Natl. Acad. Sci. USA* 94:12833–12838, 1997), and the extracts assayed for mono-, sesqui- or diterpene synthase activity with [1-$^3$H]GDP, FDP or GGDP as the respective substrate (no pentane overlay was used in assays containing GGDP). To obtain sufficient product for chromatographic analysis, the bacterial preparations were scaled to 400 mL, lysozyme was added (5 µg/mL, on ice 20 min) prior to sonication, and the resulting enzyme preparation was cleared by centrifugation as before and incubated with substrate overnight at 30° C. The terpenoid products were isolated for radio-GC and GC-MS analysis and determination of conversion rate by standard methods as previously described (Crock et al., 1997).

Instrumental Analysis

Liquid scintillation spectrometry, radio-GC and GC-MS analysis were done (Crock et al., *Proc. Natl. Acad. Sci. USA* 94:12833–12838, 1997). NMR analysis was performed on a Varian Unity Plus (599.89 MHz $^1$H, 150.85 MHz $^{13}$C) spectrometer using a Nalorac 3 mm dual $^1$H/$^{13}$C probe. The experiments were run at 21° C. with 100 µg germacrene C in 120 µL C6, D6, $^1$H and $^{13}$C chemical shifts were reported in δ (ppm) using TMS as an internal standard. All 2D data were obtained using the hypercomplex phase-sensitive method (States et al., *J. Mag. Res.* 48:286–293, 1982).

The double quantum filter homonuclear correlated spectrum was recorded with the standard pulse sequence (Rance et al., *Biochem. Biophys. Res. Commun.* 117:479–485, 1983) at a spectral window of 4181.5 Hz. The 256 t$_f$ increments of 112 scans each were sampled in 2048 complex data points. Linear prediction to the 1024 complex data points in the F$_f$ domain was used. Zero-filling to 2048 complex points in the F$_f$ domain and Gaussian weighting functions were applied in both dimensions prior to 2K×2K double Fourier transformation.

The heteronuclear multiple quantum correlation spectrum was measured with the pulse sequence (Bax et al., *J. Mag. Res.* 55:501–505, 1983) at a proton spectral window of 4181.5 Hz and carbon spectral window of 19870.8 Hz. The 512 t$_1$ increments of 256 scans each were sampled in 2048 complex data points. Linear prediction to the 2048 complex data points in the F$_1$ domain was used. Zero-filling to 4096 complex points in the F$_1$ domain and Gaussian weighting functions were applied in both dimensions prior to 2K×45K double Fourier transformation. Similar parameters were used for the heteronuclear multiple bond correlation spectrum that was acquired with the pulse sequence of Bax and Summers (Bax and Summers, *J. Am. Chem. Soc.* 108:2093–2094. 1986).

Results and Discussion

Volatile Terpenes of Tomato Leaf

Figure 2:
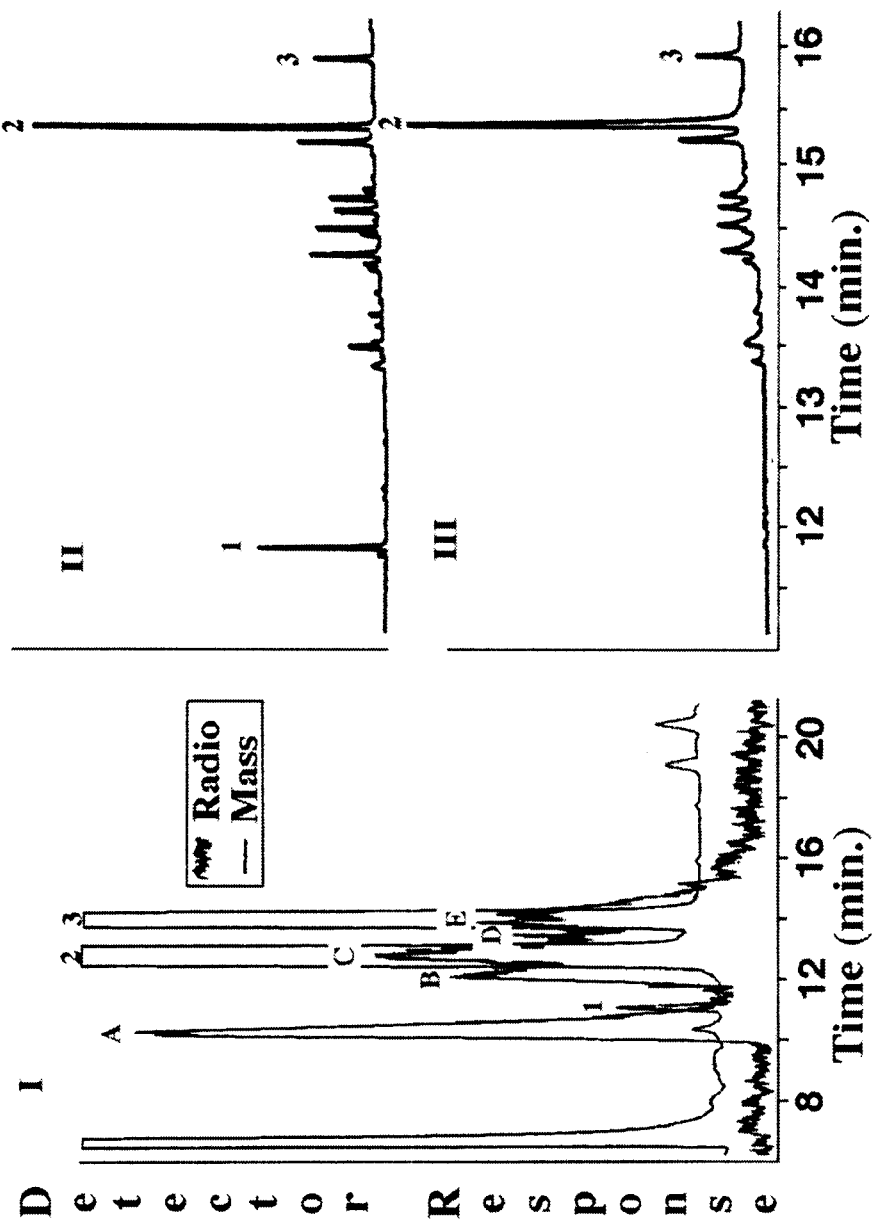
FIG. 2 shows: (I) Radio-gas chromatography (GC) analysis of the olefinic products generated from [1-$^3$H]farnesyl diphosphate (FDP) by an enzyme preparation from 'VFNT Cherry' leaves. Radiolabeled products are δ-elemene (A), β-caryophyllene (C), and α-humulene (E). The authentic standards are longifolene (1), β-caryophyllene (2), and α-humulene (3), (II) Capillary GC analysis of partially purified germacrene C with injector temperature at 230° C., and (III) the same sample with injector temperature at 40° C. The numbered peaks in II and III correspond to δ-elemene (1), germacrene C (2), and germacrene B (3).
Figure 3A:
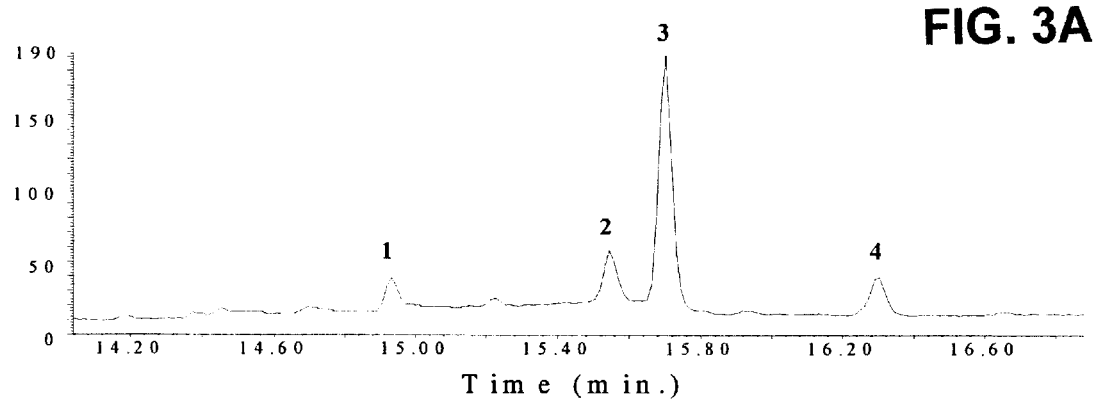
FIG. 3 shows the results of gas chromatography-mass spectrometry (GC-MS) analysis of the major products generated from farnesyl diphosphate by the recombinant germacrene C synthase. (A) Total ion chromatogram; note the rising baseline preceding germacrene C (peak 3) due to thermal decomposition to δ-elemene while on column. (B–E) Mass spectra of the sesquiterpene products generated by germacrene C synthase.
Figure 3B:
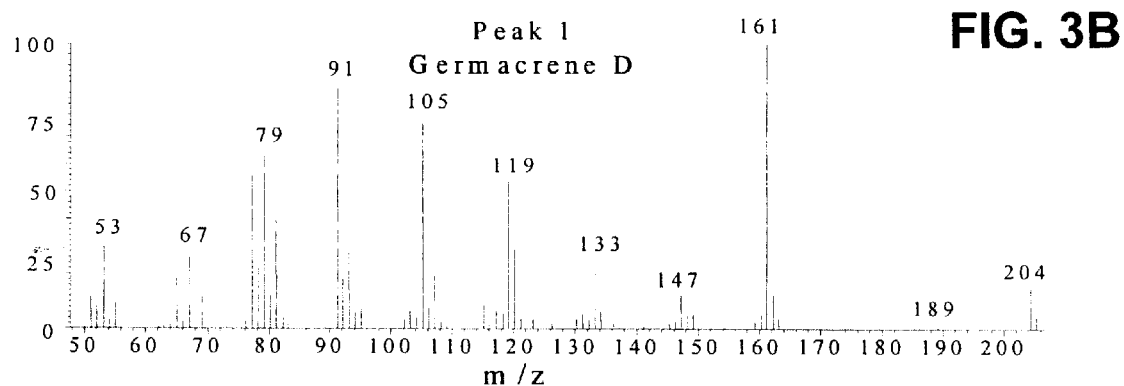
Figure 3C:
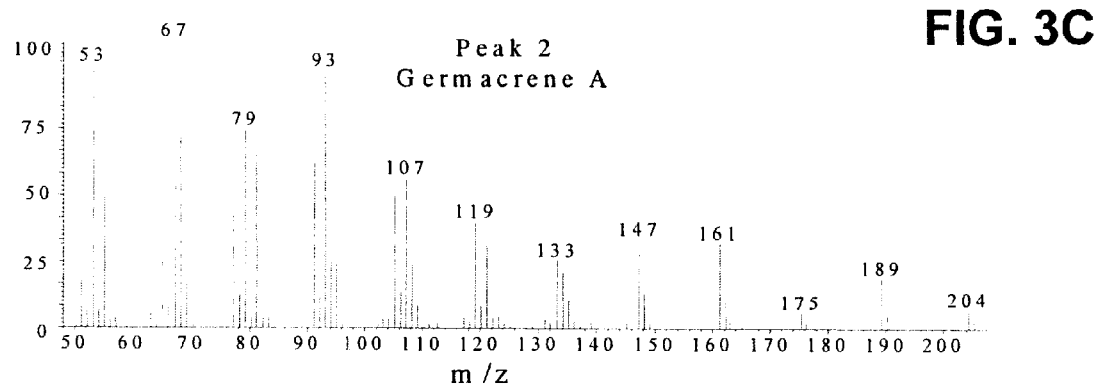
Figure 3D:
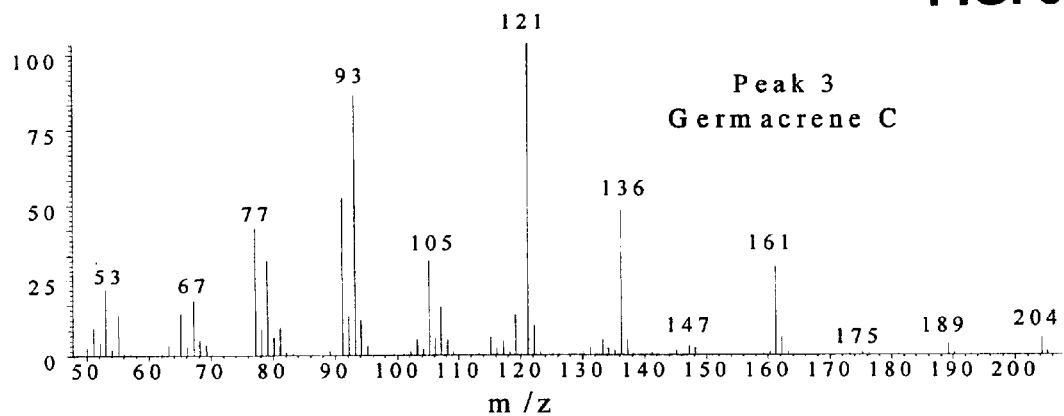
Figure 3E:
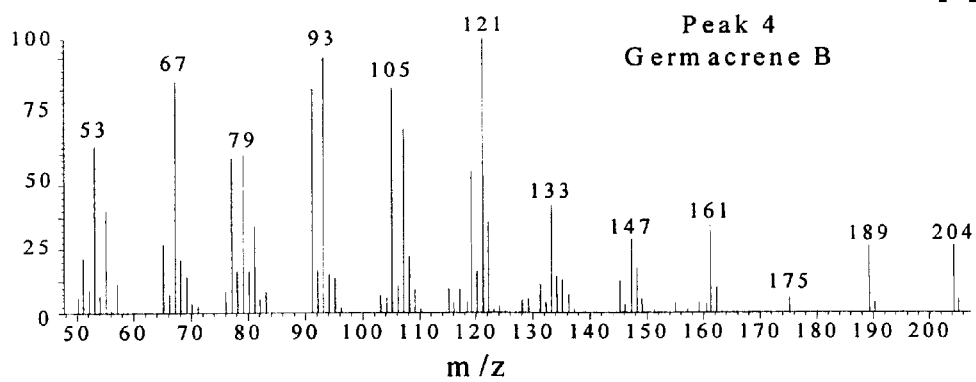

Preliminary studies, in which leaf extracts were compared to steam distillates by standard GC-MS methods (hot injector) and by cool on-column injection, revealed that the target metabolite, germacrene C (FIG. 1), was prone to thermal rearrangement to a compound with shorter GC retention time but nearly identical mass spectrum. This compound was absent in the pentane leaf extract when analyzed by cool (35° C.) on-column injection, but was present when the same pentane extract was injected onto a hot (230° C.) injector (FIG. 2). Comparison of this compound with authentic δ-elemene (FIG. 1) from black pepper oleoresin yielded an identical retention time and mass spectrum. Heating purified germacrene C in a sealed container to 130° C. for 1 h resulted in complete conversion to δ-elemene which was confirmed by GC-MS. Conversion of germacrene C to δ-elemene has been reported previously (Morikawa and Hirose, *Tetrahedron Lett.* 22:1799–1801, 1969). The sesquiterpene fraction of 'VFNT Cherry' leaves (3.2% of total volatile olefins) contained germacrene C (66%), germacrene A (7%), guaia-6,9-diene (7%), germacrene B (6%), β-caryophyllene (6%), germacrene D (4%), α-humulene (4%), and β-elemene (1%). This is the first report of azulane (guaia-6,9-diene) and germacrane skeletal types in tomatoes. By contrast, the sesquiterpene fraction of leaves from the commercial tomato variety 'Better Boy' (3.3% of total volatile olefins) contained mostly β-caryophyllene (71%), germacrene C (15%), and α-humulene (9%). The sesquiterpene composition of 'Better Boy' agrees with previous reports on the content of *L. esculentum* leaf oil (Buttery et al., *J. Agric. Food Chem.* 35:1039–1042, 1987; and Lundgren et al., *Nord. J. Bot.* 5:315–320, 1985), except that no δ-elemene was found by on-column injection; germacrene C has not been previously observed in Lycopersicon.

To confirm identity, a sample of germacrene C (>96% purity of GC) from 'VFNT Cherry' leaf oil was prepared for NMR analysis. Spectra of the putative germacrene C was consistent with the germacrene C structure. The following chemical shifts (δ) were recorded for $^{13}$C NMR (see FIG. 5 for farnesyl numbering system): C1, 122.58; C2, 130.41; C3, 127.46; C4, 40.48; C5, 28.27; C6, 125.72; C7, 141.49; C8, 40.60; C9, 32.22; C10, 145.69; C11, 37.26; C12, 22.45; C13, 22.81; C14, 21.09; C15, 16.97. Protons on these carbons produced the following δ values and multiplets: C$_{1, 6.349}$, bd, J$_{t,11}$=1.0, J$_{1,9}$=1.6; C$_{2, 5.326}$, dt, J$_{1,2}$=9.34, J$_{2,15}$=0.9; C4$^{ax}$, 1.719; C4$^{eq}$, 2.126; C5$^{ax}$, 1.954; C5$^{eq}$, 2.083; C6, 4.880; C8$^{ax}$, 1.868; C8$^{eq}$, 2.517; C9$^{ax}$, 2.355; C9$^{eq}$, 1.986; C11, 2.288; C12, 1.039; C13, 1.056; C14, 1.176, dd, J$_{14, 8eq}$=0.5; C15, 1.547.

Germacrene B was identified by GC-MS comparison with the authentic standard. Although retention times of the standard on two different columns (Alltech AT-1000 and Hewlett Packard 5MS) exactly matched those of the putative germacrene B, the mass spectrum matched γ-elemene. This apparent spectral match was noted by earlier workers (Clark et al., *J. Agric. Food Chem.* 35:514–518, 1987); however, the retention time of γ-elemene is much shorter than that of germacrene B. γ-Elemene has been previously reported from Lycopersicon (Lin et al., *J. Chem. Ecol.* 13:837–850, 1987; Buttery et al., *J. Agric. Food Chem.* 35:1039–1042, 1987; and Lundgren et al., *Nord. J. Bot.* 5:315–320, 1985), but was not found in either 'Better Boy' of 'VFNT Cherry'. Although no germacrene B was found in 'Better Boy', consistent with published analyses, it was found in 'VFNT Cherry', constituting the first report of this compound in tomato.

The monoterpene composition of 'VFNT Cherry' leaves was quantitatively and qualitatively very similar to that of 'Better Boy' leaves. Leaves of both cultivars contained monoterpenes as the principal volatile olefines (91.4%), with β-phellandrene (52% of total) followed by 2-carene (16%) and limonene (10%) as the most abundant components (FIG. 1). The monoterpene content of *L. esculentum* has been examined previously in some detail (Buttery et al., *J. Agric. Food Chem.* 35:1039–1042, 1987; and Lundgren et al., *Nord. J. Bot.* 5:315–320, 1985).

Sesquiterpene Synthase Activity in Leaf Extracts

To examine the origin of the germacrenes, a soluble protein extract was prepared from young 'VFNT Cherry' leaves and assayed for sesquiterpene synthases employing [1-$^3$H]FDP as substrate. Radio-GC analysis (250° C. injector) of the sesquiterpene olefins generated (ca. 3% conversion of substrate) revealed the presence of tritium-labeled olefins coincident with δ-elemene (33%), caryophyllene (22%), and humulene (19%), with at least two other sesquiterpenes (total of 26%) (FIG. 2). None of these cyclic olefins was produced in boiled controls, confirming their enzymatic origin. The formation of these products was dependent on the presence of the divalent metal ion cofactors, consistent with the established behavior of all known sesquiterpene synthases (Cane, *Chem. Rev.* 90:1089–1103, 1990). No oxygenated sesquiterpenoids were produced from [1-$^3$H]FDP, other than farnesol and nerolidol (minor), which were derived via endogenous phosphatases and/or non-enzymatic solvolysis. Caryophyllene and humulene oxides have been reported in tomato leaves (Buttery et al., *J. Agric. Food Chem.* 35:1039–1042, 1987), but these metabolites are likely formed by subsequent oxygenation of the corresponding olefins. This is the first report on the sesquiterpene synthases of Lycopersicon, which yield olefinic products consistent with the volatile oil content of 'VFNT Cherry' leaves.

Terpenoid Synthase cDNA Isolation and Characterization

Using 'VFNT Cherry' leaf library cDNA as template, the two degenerate PCR primers amplified a gene fragment of the expected size. This 767-bp fragment was shown to resemble TEAS (74% identity) and vetispiradiene synthase (78% identity) (Facchini and Chappell, *Proc. Natl. Acad. Sci. USA* 89:11088–11092, 1992; and Back and Chappell, *J. Biol. Chem.* 270:7375–7381, 1995), two sesquiterpene cyclases from related solanaceous plants. Southern blot hybridization of the PCR product to multiply restricted 'VFNT Cherry' and spearmint (control) DNA revealed that the probe hybridized to three or four bands of tomato DNA, suggesting a small gene family; the probe did not recognize the spearmint DNA control.

From high-stringency screening of the tomato cDNA library, 31 positive clones were isolated. Restriction mapping indicated all clones to be representatives of the same gene family, and 16 of these phagemids containing inserts over 1.8 kb in length were used to transform *E. coli*. Nine clones (pLE7.1, pLE11.3, pLE12.1, pLE14.1, pLE14.2, pLE15.4, pLE16.3, pLE17.5, and pLE20.3) expressed sesquiterpene synthase activity capable of converting [1-$^3$H] FDP to radiolabeled olefin(s); clones pLE11.3 and pLE14.2 were most active, followed by clone pLE20.3. Radio-GC analysis of the products of all active clones revealed the same pattern of sesquiterpene olefins. Detailed GC-MS analysis of the products generated by clones pLE11.3, pLE14.2, and pLE20.3 confirmed the identical distribution pattern and permitted the identification of germacrene C (64%), germacrene A (18%), germacrene B (11%) and germacrene D (7%) (FIG. 3), all products that were identified in the volatile fraction of 'VFNT Cherry' leaves or generated in the cell-free assay. However, due to the thermal decomposition of germacrene C while on column (note the rising baseline preceding germacrene C elution in FIG. 3), the amount of germacrene C actually produced may be twice that indicated. Control experiments established that sesquiterpene formation from FDP in extracts of transformed *E. coli* was insert-dependent, and required divalent cation, substrate, and functional enzyme (boiled extracts were inactive). The only oxygenated sesquiterpenes generated in transformed *E. coli* preparations were farnesol and nerolidol, derived via endogenous phosphatases and/or non-enzymatic solvolysis; the formation of both was independent of the cDNA insert. Although caryophyllene and humulene are present in the volatile complex of 'VFNT Cherry' leaves, and are produced from FDP by extracts of this tissue, neither sesquiterpene was produced in detectable amounts by the recombinant enzyme. Therefore, these products must arise from a different synthase(s).

None of the clones expressed detectable diterpene synthase activity with GGDP as substrate. Only one germacrene C synthase clone, pLE11.3, yielded a protein capable of converting [1-$^3$H]GDP to a monoterpene product identified as limonene by radio-GC analysis. The germacrene synthase activity expressed from clone pLE11.3 exceeded the limonene synthase activity by a factor of ten when measured in the same enzyme preparation at saturating levels of the corresponding prenyl diphosphate substrate and Mg$^{++}$ cofactor. Sequence analysis (see below) provided a rationale for this observation of bifunctional cyclization activity.

Sequence Analysis

Clones pLE11.3, pLE14.2 and pLE20.3 were selected for complete nucleotide-sequence analysis based on functional expression and comparatively large insert size. These cDNAs are 1948, 2022 and 1878 bp in length, respectively, and contain single open reading frames of 1622, 1647, and 1647 bp, respectively. Clones pLE11.3 and pLE 14.2 contain the longest 3'-untranslated regions, but shorter 5'-untranslated regions than does pLE20.3. Clones pLE14.2 and pLE20.3 are in different reading frames with respect to the vector β-galactosidase start site; however, each contains a stop codon (−12 and −29 nucleotides from the initial cDNA ATG, respectively) in the 5'-untranslated region that is in frame with the β-galactosidase start site. Both pLE14.2 and pLE20.3 inserts contain at the start site a purineXX-AUGG motif that provides high recognition as a secondary start site in polycistronic messages. Thus, it is likely that the germacrene synthases dried from these clones are translated as proteins free of vector-derived peptide, and that their apparent difference in enzyme activity (3-fold) is probably due to the extra distance the ribosome must traverse to locate the second start site in the pLE20.3 message compared to that of pLE14.2, resulting in lower translation efficiency.

The nucleotide sequence of pLE20.3 is shown in FIG. 6 (SEQ ID NO:1). The nucleotide-sequence of pLE14.2 is shown in FIG. 8 (SEQ ID NO:3). Clones pLE20.3 and pLE14.2 bear several single-base differences that result in four amino acid changes near the carboxy terminus (FIG. 4; SEQ ID NO:2). Since 'VFNT Cherry' is a $F_5$ selection, and therefore not entirely homozygous, it is unclear whether pLE20.3 and pLE14.2 represent different alleles or different transcripts derived from two germacrene C synthase loci.

The only clone capable of expressing a monoterpene (limonene) synthase activity (pLE11.3) is truncated by 25 nucleotides into the 5'-end of the open reading frame, thereby deleting the starting methionine and the following seven residues, and also changing the ninth residue. The cDNA sequence for the remaining open reading frame is identical to that of clone pLE20.3 which does not express detectable monoterpene synthase activity. The first residue (Arg) encoded entirely by the pLE11.3 cDNA insert is also the first conserved residue among the known plant terpenoid synthases, and this codon is in frame with the vector β-galactosidase start site. Thus, the expressed product derived from pLE11.3 is probably a fusion protein in which the amino-terminally truncated germacrene synthase is fused to a 42 residue, vector-derived peptide. The ability of clone pLE11.3 to express limonene synthase activity with GDP as substrate is apparently the result of this cloning artifact, and so is not relevant to limonene production in vivo. The utilization of GDP as an alternate substrate by a sesquiterpene synthase has been reported for three other plant sesquiterpene synthases (Crock et al., *Proc. Natl. Acad. Sci. USA* 94:12833–12838, 1997; and Steele et al., *J. Biol Chem*. 273:2078–2089, 1998) that are apparently translated in the native form; however, this is the first report in which substrate utilization is altered by modification of the N-terminus. Back and Chappell (Back and Chappell, *Proc. Natl. Acad. Sci. USA* 93:6841–6845, 1996) have conducted domain-swapping experiments in which domains from TEAS were switched with domains from vetispiradiene synthase. They found that chimeric enzymes with new product compositions could be produced; however, they dd not test these hybrid enzymes for acceptance of alternate substrates (either GDP or GGDP).

Comparison of the deduced amino acid sequences (FIGS. 4 and 7; SEQ ID NO:2) of clone pLE20.3 with those of other plant sesquitepene synthases reveals a significant degree of similarity. The sequence of tomato germacrene C synthase is most similar to δ-cadinene synthase from cotton (Malvaceae) in showing 68% similarity and 50% identity (Chen et al., *Arch. Biochem. Biophys*. 324:255–266, 1996). The defined sesquiterpene synthases from other solanaceous plants, vetispiradiene synthase from *Hyoscyamus muticus* (Back and Chappell, *J. Biol. Chem*. 270:7375–7381, 1995) and TEAS (Facchini and Chappell, *Proc. Natl. Acad. Sci. USA* 89:11088–11092, 1992), each exhibit 65% similarity and 45% identity to germacrene C synthase at the amino acid level. Germacrene C synthase is least like (E)-β-farnesene synthase form peppermint (45% similarity, 34% identity) (Crock et al., *Proc. Natl. Acad. Sci. USA* 94;12833–12838, 1997) and δ-selinene and γ-humulene synthases from grand fir (41% similarity and 29% identity, and 54% similarity and 27% identity, respectively) (Steele et al., *J. Biol. Chem*. 273:2078–2089, 1998). It is interesting that, although the reaction mechanisms of TEAS, vetispiradiene synthase, and δ-selinene synthase have all been postulated to proceed through a germacrene intermediate (Steele et al., *J. Biol. Chem*. 273:2078–2089, 1998; Back and Chappell, *Proc. Natl. Acad. Sci. USA* 93:6841–6845, 1996), these are not more similar to germacrene C synthase in sequence than are other known sesquiterpene synthases (Steele et al., *J. Biol. Chem*. 273:2078–2089; and Chen et al., *Arch. Biochem. Biophys*. 324:255–266, 1996) which produce structurally unrelated products.

As is typical of the sesquiterpene synthases of plant origin (Crock et al., *Proc. Natl Acad. Sci. USA* 94:12833–12838, 1997; Facchini and Chappell, *Proc. Natl. Acad. Sci. USA* 89:11088–11092, 1992; Back and Chappell, *J. Biol. Chem*. 270:7375–7381, 1995; Steele et al., *J. Biol. Chem*. 273:2078–2089, 1998; and Chen et al., *Arch. Biochem. Biophys*. 324:255–266, 1996), tomato germacrene C synthase appears to lack an amino terminal organelle-targeting sequence. Therefore, the enzyme must be directed to the cytoplasm which is the site of sesquiterpene biosynthesis; monoterpenes and diterpenes are synthesized in plastids (Colby et al., *J. Biol. Chem*. 268:23016–23024, 1993). Translation of the germacrene synthase cDNA yields a deduced protein of 64,114 daltons with a pI of 5.82. The aspartate-rich motif (DDXXD) found in most prenyltransferases and terpenoid cyclases, and thought to play a role in substrate binding (Marrero et al., *J. Biol. Chem*. 267:21873–21878, 1992), is also present in germacrene C synthase (FIG. 4; SEQ ID NO:2).

Cyclization Mechanism

Figure 5:
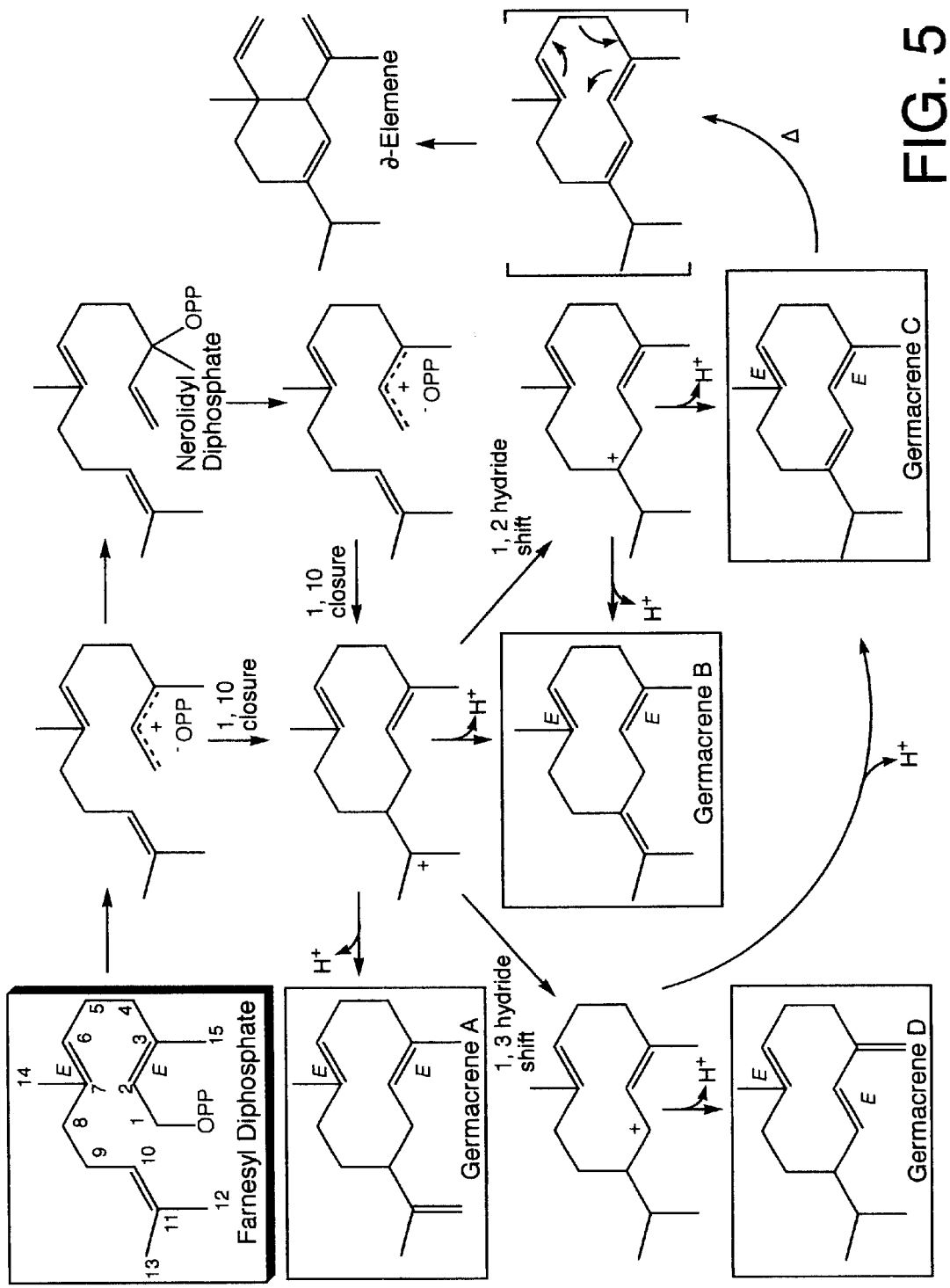

Germacrene C synthase from tomato, like many other terpenoid cyclases of plant origin (Crock et al., *Proc. Natl. Acad. Sci. USA* 94:12833–12838, 1997; and Steele et al.,*J. Biol. Chem*. 273:2078–2089, 1998), is capable of producing multiple reaction products, probably as a consequence of the highly reactive carbocationic intermediates that are generated from FDP (Cane, *Chem. Rev*. 90:1089–1103, 1990). The electrophilic cyclization reaction is postulated to proceed by the initial ionization of the diphosphate ester (FIG. 5). Capture of the diphosphate anion at C3 of the resulting carbocation may occur to form nerolidyl diphosphate which may simply re-ionize to the original transoid carbocation to permit C1,C10-closure to the germacryl skeleton.

Two alternatives for deprotonation of the $C_{10}$ macrocyclic carbocation yield germacrene A or B. A 1,3-hydride shift in the macrocycle and deprotonation by two alternate routes produced germacrenes D or C, while a 1,2 -hydride shift with alternative deprotonations can generate germacrenes C or B. Upon heating, germacrene C undergoes Cope rearrangement to δ-elemene (see FIG. 2 and FIG. 5). Similarly, β-elemene is the Cope-rearrangement product of germacrene A. Although β-elemene was not observed as a biosynthetic product of germacrene C synthase, this olefin was detected in 'VFNT Cherry' leaf volatiles. γ-Elemene (the Cope-rearrangement product of germacrene B) was not detected either as a biosynthetic product or a metabolite of 'VFNT Cherry' leaves.

Recently, the crystal structure of TEAS has been solved (Starks et al., *Science* 277:1815–1820, 1997) and detailed sequence comparison with germacrene C synthase may reveal the structural basis for many of the catalytic steps in germacrene formation. In TEAS, upon binding and subsequent ionization of FDP, closure of an α-helical loop over the active site is facilitated by interactions between $Trp^{273}$ and $Tyr^{527}$ to form a pocket that shields the resulting carbocation intermediate from quenching by solvent water. These two residues are conserved as $Trp^{272}$ and $Tyr^{527}$ in germacrene C synthase and, assuming a common synthase folding (Starks et al., *Science* 277:1815–1820, 1997), they likely play an identical role. Loop closure also positions residues $Arg^{264}$ and $Arg^{441}$ of the aristolochene synthase near C1 of the substrate and thus, along with the coordination of substrate-bound metal ions by the DDXXD motif, helps direct the metal ion-chelated diphosphate anion away from the newly formed carbocation. These basic residues are conserved as $Arg^{263}$ and $Arg^{442}$ in the germacrene synthase. Several of the backbone carbonyls and $Thr^{403}$ direct attack of C10 on the $C_1$ cationic center to form a germacryl intermediate in the aristolochene synthase.

Although there is no direct homolog of $Thr^{403}$ in the germacrene synthase (only $Ser^{401}$), positioning of $Tyr^{527}$ (in both synthases) near C11 stabilizes the macrocyclic carbocation formed and allows $Asp^{525}$ (in both synthases) to deprotonate at C13 to yield germacrene A. In the germacrene synthase, several lysine residues upstream of $Asp^{525}$ may discourage proton elimination and permit the hydride shift (s) needed to generate germacrenes C and D. In TEAS, reprotonation of the germacrene intermediate at C6 to yield the bicyclic eudesmane nucleus is facilitated by a catalytic triad of $Asp^{444}$, $Tyr^{520}$, and $ASp^{525}$. The protonation cycle is initiated by $Asp^{444}$, and the cationic center formed at C3 after ring closure is stabilized by the hydroxyl of $Thr^{403}$. No reprotonation of germacrene can occur in the germacrene synthase because the initiating aspartate has been altered to $Asn^{445}$, and the hydroxyl of $Ser^{401}$ may be too distant to stabilize the developing positive charge on C3; thus, the macrocyclic germacrenes are released as terminal products. With the development of an efficient functional expression system for germacrene C synthase, these mechanistic inferences can be tested by mutagenesis and the structure of the enzyme examined directly. The isolation of the germacrene C synthase cDNA also provides the means for genetic engineering of sesquiterpenoid-based plant defenses and refines the development of probes for identification of other terpenoid synthases in tomato.

This invention has been detailed both by example and by direct description. It should be apparent that one having ordinary skill in the relevant art would be able to surmise equivalents to the invention as described in the claims which follow but which would be within the spirit of the foregoing description. Those equivalents are to be included within the scope of this invention.

What is claimed is:

1. A purified protein having germacrene C synthase biological activity, and comprising an amino acid sequence selected from the group consisting of::
   (a) the amino acid sequence of SEQ ID NO:2; and
   (b) amino acid sequences having at least 70% sequence identity with the sequence of SEQ ID NO:2.

2. An isolated nucleic acid molecule encoding a protein according to claim 1.

3. A recombinant nucleic acid comprising a promoter sequence operably linked to the nucleic acid sequence according to claim 2.

4. A cell transformed with a recombinant nucleic acid according to claim 3.

5. A transgenic plant comprising the recombinant nucleic acid according to claim 3.

6. A transgenic plant according to claim 5, wherein the plant is selected form the group consisting of angiosperms and gymnosperms.

7. A transgenic plant according to claim 5 wherein the plant is selected from the group consisting of: tomato, tobacco, pepper, broccoli, cauliflower, cabbage, cowpea, grape, rape, bean, soybean, rice, corn, wheat, barley, rye, citrus, cotton, cassava and walnut, wherein the transgenic plant displays enhanced pathogen resistance when compared to a non-transgenic, but otherwise similar plant.

8. An isolated nucleic acid that:
  (a) hybridizes with the nucleotide sequence of SEQ ID NO:1 to form a hybrid pair, wherein hybridization conditions comprise at least 3xSSC, a temperature of between 12° C. and 20° C. below the calculated melting temperature of the hybrid pair, and a hybridization time of at least 4 hours; and wash conditions comprise 2xNaCl—NaH$_2$PO$_4$—EDTA and 0.5% SDS for 20 minutes at a temperature of between 12° C. and 20° C. below the calculated melting temperature of the hybrid pair; and
  (b) encodes a protein having germacrene C synthase biological activity.

9. The isolated nucleic acid of claim 8 that hybridizes with said nucleic acid probe under hybridization conditions of at least 3xSSC at 65° C. for at least 4 hours, and wash conditions of 2xNaCl—NaH$_2$PO$_4$-EDTA and 0.5% SDS for 20 minutes at 65° C.

10. An isolated nucleic acid encoding a protein with germacrene C biological activity, wherein the nucleic acid has at least 70% sequence identity with the open reading frame of the germacrene C synthase cDNA of SEQ ID NO:1.

* * * * *

UNITED STATES PATENT AND TRADEMARK OFFICE
CERTIFICATE OF CORRECTION

PATENT NO. : 6,342,380 B1
DATED : January 29, 2002
INVENTOR(S) : Colby et al.

It is certified that error appears in the above-identified patent and that said Letters Patent is hereby corrected as shown below:

Title page,
Item [73], Assignees, "Washington State Research Foundation" should be
-- Washington State University Research Foundation --.

Column 4,
Line 41, "FIG. 3" should be -- FIG. 5 --.

Column 9,
Line 24, a comma -- , -- should be inserted between "vegetables" and "berries".

Column 12,
Line 19, the semi-colon ";" after "residue" should be a comma -- , --.

Column 14,
Line 52, "liquids" should be -- lipids --.
Line 59, "isolate" should be -- isolated --.

Column 16,
Line 54, "an et al." should be -- An et al. --.

Column 17,
Line 60, "($M_f$=ca. 40,000)" should be -- ($M_r$=ca. 40,000) --.

Column 18,
Line 27, the period "." after "primers" should be deleted.
Line 32, "5'-T(C)TG(T)CATA(G)TAA(G)TCIGG(A)LAG-3']" should be
-- 5'-T(C)TG(T)CATA(G)TAA(G)TCIGG(A)IAG-3'] --.
Line 36, "$\mu$cDNA" should be -- $\mu$g cDNA --.

Column 19,
Line 35, a comma -- , -- should be inserted after "sesqui- ".
Line 54, "C6, D6," should be -- $C_6$, $D_6$. --.

Column 20,
Line 9, "2Kx45K" should be -- 2Kx4K --.
Line 60, "$J_{t,11}$=1.0" should be -- $J_{1,11}$=1.0 --.
Line 60, "$J_{1,9}$=1.6" should be -- $J_{1,9}$=1.6 --.

UNITED STATES PATENT AND TRADEMARK OFFICE
CERTIFICATE OF CORRECTION

PATENT NO. : 6,342,380 B1
DATED : January 29, 2002
INVENTOR(S) : Colby et al.

It is certified that error appears in the above-identified patent and that said Letters Patent is hereby corrected as shown below:

Column 21,
Line 10, "of" should be -- or --.

Column 22,
Line 49, a comma -- , -- should be inserted after "2022".

Column 23,
Line 40, "dd" should be -- did --.
Line 54, "65%" should be -- 64% --.
Line 60, "54%" should be -- 40% --.

Column 25,
Line 6, "$C_1$" should be -- C1 --.
Line 18, "$ASp^{525}$" should be -- $Asp^{525}$ --.

Signed and Sealed this

Fifth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,342,380 B1
DATED : January 29, 2002
INVENTOR(S) : Colby et al.

It is certified that error appears in the above-identified patent and that said Letters Patent is hereby corrected as shown below:

Column 1,
Lines 10-18, the section entitled "Acknowledgement of Government Support" should be replaced with the following:
-- Acknowledgement of Government Support:
This invention was made with government support under U.S. Department of Agriculture NRI Grant 93-37301-9504, U.S. Department of Agriculture ARC Contingency Funds for Whitefly Research, National Institutes of Health Grant GM31354, and National Science Foundation Grant 9104983. The government has certain rights in this invention. --

Signed and Sealed this

Thirteenth Day of April, 2004

JON W. DUDAS
*Acting Director of the United States Patent and Trademark Office*

SEQUENCE LISTING

<160> NUMBER OF SEQ ID NOS: 6

<210> SEQ ID NO 1
<211> LENGTH: 1879
<212> TYPE: DNA
<213> ORGANISM: Lycopersicon esculentum
<220> FEATURE:
<221> NAME/KEY: CDS
<222> LOCATION: (39)..(1685)

<400> SEQUENCE: 1

```
gaagcttgaa aaaaagcaaa ccttagaaca aacaagca atg gct gct tct tct gct     56
                                          Met Ala Ala Ser Ser Ala
                                          1               5 gat aag tgt cgc ccc ttg gct aat ttt cac cca tct gtt tgg gga tat    104
Asp Lys Cys Arg Pro Leu Ala Asn Phe His Pro Ser Val Trp Gly Tyr
            10                  15                  20 cat ttc ctt tct tat act cat gaa att act aat caa gaa aaa gtt gaa    152
His Phe Leu Ser Tyr Thr His Glu Ile Thr Asn Gln Glu Lys Val Glu
        25                  30                  35 gtt gat gag tac aaa gag aca att aga aaa atg ctg gtg gaa act tgc    200
Val Asp Glu Tyr Lys Glu Thr Ile Arg Lys Met Leu Val Glu Thr Cys
    40                  45                  50 gac aat agc act caa aag ctt gtg ttg ata gac gcg atg caa cga ttg    248
Asp Asn Ser Thr Gln Lys Leu Val Leu Ile Asp Ala Met Gln Arg Leu
55                  60                  65                  70 gga gtg gct tat cat ttc gat aat gaa att gaa aca tcc att caa aac    296
Gly Val Ala Tyr His Phe Asp Asn Glu Ile Glu Thr Ser Ile Gln Asn
                75                  80                  85 att ttt gat gca tcg tcc aaa cag aat gat aat gac aac aac ctt tac    344
Ile Phe Asp Ala Ser Ser Lys Gln Asn Asp Asn Asp Asn Asn Leu Tyr
            90                  95                 100 gtt gtg tct ctt cgt ttt cga ctt gtg agg caa caa ggc cat tac atg    392
Val Val Ser Leu Arg Phe Arg Leu Val Arg Gln Gln Gly His Tyr Met
        105                 110                 115 tct tca gat gtg ttc aag caa ttc acc aac caa gat ggg aaa ttc aag    440
Ser Ser Asp Val Phe Lys Gln Phe Thr Asn Gln Asp Gly Lys Phe Lys
    120                 125                 130 gaa aca ctt act aat gat gtc caa gga tta ttg agt ttg tat gaa gca    488
Glu Thr Leu Thr Asn Asp Val Gln Gly Leu Leu Ser Leu Tyr Glu Ala
```

```
                                                                      -continued
135                 140                 145                 150
tca cat ctg aga gtg cgt aat gag gag att ctt gaa gaa gct ctt aca          536
Ser His Leu Arg Val Arg Asn Glu Glu Ile Leu Glu Glu Ala Leu Thr
                155                 160                 165 ttt acc acc act cat ctc gag tct att gtc tcc aac ttg agc aat aat          584
Phe Thr Thr Thr His Leu Glu Ser Ile Val Ser Asn Leu Ser Asn Asn
                170                 175                 180 aat aac tct ctt aag gtt gaa gtt ggt gaa gcc tta act cag cct att          632
Asn Asn Ser Leu Lys Val Glu Val Gly Glu Ala Leu Thr Gln Pro Ile
                185                 190                 195 cgc atg act tta cca agg atg gga gct aga aaa tac ata tcc att tac          680
Arg Met Thr Leu Pro Arg Met Gly Ala Arg Lys Tyr Ile Ser Ile Tyr
                200                 205                 210 gaa aac aat gat gca cac cac cat ttg ctt ttg aaa ttt gct aaa ttg          728
Glu Asn Asn Asp Ala His His His Leu Leu Leu Lys Phe Ala Lys Leu
215                 220                 225                 230 gat ttt aac atg ctg caa aag ttt cac caa aga gag ctt agt gat ctt          776
Asp Phe Asn Met Leu Gln Lys Phe His Gln Arg Glu Leu Ser Asp Leu
                235                 240                 245 aca agg tgg tgg aaa gat ttg gat ttt gca aat aaa tat cca tat gca          824
Thr Arg Trp Trp Lys Asp Leu Asp Phe Ala Asn Lys Tyr Pro Tyr Ala
                250                 255                 260 aga gac agg ttg gtt gag tgt tac ttc tgg ata tta gga gtg tat ttt          872
Arg Asp Arg Leu Val Glu Cys Tyr Phe Trp Ile Leu Gly Val Tyr Phe
                265                 270                 275 gag cca aaa tat agt cgt gcg aga aaa atg atg aca aaa gta ctc aac          920
Glu Pro Lys Tyr Ser Arg Ala Arg Lys Met Met Thr Lys Val Leu Asn
280                 285                 290 ctg acc tcc att att gac gac act ttt gat gct tat gca acc ttt gac          968
Leu Thr Ser Ile Ile Asp Asp Thr Phe Asp Ala Tyr Ala Thr Phe Asp
295                 300                 305                 310 gaa ctt gtg act ttc aat gat gca atc cag aga tgg gat gct aat gca         1016
Glu Leu Val Thr Phe Asn Asp Ala Ile Gln Arg Trp Asp Ala Asn Ala
                315                 320                 325 att gat tca ata caa cca tat atg aga cct gct tat caa gct ctt cta         1064
Ile Asp Ser Ile Gln Pro Tyr Met Arg Pro Ala Tyr Gln Ala Leu Leu
                330                 335                 340 gac att tac agt gaa atg gaa caa gtg ttg tcc aaa gaa ggt aaa ctg         1112
Asp Ile Tyr Ser Glu Met Glu Gln Val Leu Ser Lys Glu Gly Lys Leu
                345                 350                 355 gac cgt gta tac tat gca aaa aat gag atg aaa aag ttg gtg aga gcc         1160
Asp Arg Val Tyr Tyr Ala Lys Asn Glu Met Lys Lys Leu Val Arg Ala
                360                 365                 370 tat ttt aag gaa acc caa tgg ttg aat gat tgt gac cat att cca aaa         1208
Tyr Phe Lys Glu Thr Gln Trp Leu Asn Asp Cys Asp His Ile Pro Lys
375                 380                 385                 390 tat gag gaa caa gtg gag aat gca atc gta agt gct ggc tat atg atg         1256
Tyr Glu Glu Gln Val Glu Asn Ala Ile Val Ser Ala Gly Tyr Met Met
                395                 400                 405 ata tca aca act tgc ttg gtc ggt ata gaa gaa ttt ata tcc cac gag         1304
Ile Ser Thr Thr Cys Leu Val Gly Ile Glu Glu Phe Ile Ser His Glu
                410                 415                 420 act ttt gaa tgg ttg atg aat gag tct gtg att gtt cga gct tcc gca         1352
Thr Phe Glu Trp Leu Met Asn Glu Ser Val Ile Val Arg Ala Ser Ala
                425                 430                 435 ttg att gcc aga gca atg aac gat att gtt gga cat gaa gat gaa caa         1400
Leu Ile Ala Arg Ala Met Asn Asp Ile Val Gly His Glu Asp Glu Gln
                440                 445                 450 gaa aga gga cat gta gct tca ctt att gaa tgt tac atg aaa gat tat         1448
```

-continued

```
Glu Arg Gly His Val Ala Ser Leu Ile Glu Cys Tyr Met Lys Asp Tyr
455                 460                 465                 470 gga gct tca aag caa gag act tac att aag ttc ctg aaa gag gtc acc     1496
Gly Ala Ser Lys Gln Glu Thr Tyr Ile Lys Phe Leu Lys Glu Val Thr
                475                 480                 485 aat gca tgg aag gac ata aac aaa caa ttc ttc cgt cca act gaa gta     1544
Asn Ala Trp Lys Asp Ile Asn Lys Gln Phe Phe Arg Pro Thr Glu Val
            490                 495                 500 cca atg ttt gtc ctt gaa cga gtt cta aat ttg aca cgt gtg gct gac     1592
Pro Met Phe Val Leu Glu Arg Val Leu Asn Leu Thr Arg Val Ala Asp
        505                 510                 515 acg tta tat aaa gag aaa gat aca tat aca aac gcc aaa gga aaa ctt     1640
Thr Leu Tyr Lys Glu Lys Asp Thr Tyr Thr Asn Ala Lys Gly Lys Leu
    520                 525                 530 aaa aac atg att aat tca ata cta att gaa tct gtc aaa ata taa         1685
Lys Asn Met Ile Asn Ser Ile Leu Ile Glu Ser Val Lys Ile
535                 540                 545 atataatgct gaaattgcac cttcatcatt caactattca cagcaaaata aggcatataa   1745
taaattgaag actcacaaca tatgagttgt taattcctgg gatgtttgaa ataaacaata   1805
attgttttta tttaatttgc taagcaaaag tgaaatatac aacacttgag ttgtattaaa   1865
aaaaaaaaaa aaaa                                                     1879

<210> SEQ ID NO 2
<211> LENGTH: 548
<212> TYPE: PRT
<213> ORGANISM: Lycopersicon esculentum

<400> SEQUENCE: 2

Met Ala Ala Ser Ser Ala Asp Lys Cys Arg Pro Leu Ala Asn Phe His
  1               5                  10                  15

Pro Ser Val Trp Gly Tyr His Phe Leu Ser Tyr Thr His Glu Ile Thr
            20                  25                  30

Asn Gln Glu Lys Val Glu Val Asp Glu Tyr Lys Glu Thr Ile Arg Lys
        35                  40                  45

Met Leu Val Glu Thr Cys Asp Asn Ser Thr Gln Lys Leu Val Leu Ile
     50                  55                  60

Asp Ala Met Gln Arg Leu Gly Val Ala Tyr His Phe Asp Asn Glu Ile
 65                  70                  75                  80

Glu Thr Ser Ile Gln Asn Ile Phe Asp Ala Ser Ser Lys Gln Asn Asp
                 85                  90                  95

Asn Asp Asn Asn Leu Tyr Val Val Ser Leu Arg Phe Arg Leu Val Arg
            100                 105                 110

Gln Gln Gly His Tyr Met Ser Ser Asp Val Phe Lys Gln Phe Thr Asn
        115                 120                 125

Gln Asp Gly Lys Phe Lys Glu Thr Leu Thr Asn Asp Val Gln Gly Leu
    130                 135                 140

Leu Ser Leu Tyr Glu Ala Ser His Leu Arg Val Arg Asn Glu Glu Ile
145                 150                 155                 160

Leu Glu Glu Ala Leu Thr Phe Thr Thr Thr His Leu Glu Ser Ile Val
                165                 170                 175

Ser Asn Leu Ser Asn Asn Asn Asn Ser Leu Lys Val Glu Val Gly Glu
            180                 185                 190

Ala Leu Thr Gln Pro Ile Arg Met Thr Leu Pro Arg Met Gly Ala Arg
        195                 200                 205

Lys Tyr Ile Ser Ile Tyr Glu Asn Asn Asp Ala His His His Leu Leu
```

```
              210                 215                 220
Leu Lys Phe Ala Lys Leu Asp Phe Asn Met Leu Gln Lys Phe His Gln
225                 230                 235                 240

Arg Glu Leu Ser Asp Leu Thr Arg Trp Trp Lys Asp Leu Asp Phe Ala
                245                 250                 255

Asn Lys Tyr Pro Tyr Ala Arg Asp Arg Leu Val Glu Cys Tyr Phe Trp
                260                 265                 270

Ile Leu Gly Val Tyr Phe Glu Pro Lys Tyr Ser Arg Ala Arg Lys Met
                275                 280                 285

Met Thr Lys Val Leu Asn Leu Thr Ser Ile Ile Asp Asp Thr Phe Asp
                290                 295                 300

Ala Tyr Ala Thr Phe Asp Glu Leu Val Thr Phe Asn Asp Ala Ile Gln
305                 310                 315                 320

Arg Trp Asp Ala Asn Ala Ile Asp Ser Ile Gln Pro Tyr Met Arg Pro
                325                 330                 335

Ala Tyr Gln Ala Leu Leu Asp Ile Tyr Ser Glu Met Glu Gln Val Leu
                340                 345                 350

Ser Lys Glu Gly Lys Leu Asp Arg Val Tyr Tyr Ala Lys Asn Glu Met
                355                 360                 365

Lys Lys Leu Val Arg Ala Tyr Phe Lys Glu Thr Gln Trp Leu Asn Asp
370                 375                 380

Cys Asp His Ile Pro Lys Tyr Glu Glu Gln Val Glu Asn Ala Ile Val
385                 390                 395                 400

Ser Ala Gly Tyr Met Met Ile Ser Thr Thr Cys Leu Val Gly Ile Glu
                405                 410                 415

Glu Phe Ile Ser His Glu Thr Phe Glu Trp Leu Met Asn Glu Ser Val
                420                 425                 430

Ile Val Arg Ala Ser Ala Leu Ile Ala Arg Ala Met Asn Asp Ile Val
                435                 440                 445

Gly His Glu Asp Glu Gln Glu Arg Gly His Val Ala Ser Leu Ile Glu
450                 455                 460

Cys Tyr Met Lys Asp Tyr Gly Ala Ser Lys Gln Glu Thr Tyr Ile Lys
465                 470                 475                 480

Phe Leu Lys Glu Val Thr Asn Ala Trp Lys Asp Ile Asn Lys Gln Phe
                485                 490                 495

Phe Arg Pro Thr Glu Val Pro Met Phe Val Leu Glu Arg Val Leu Asn
                500                 505                 510

Leu Thr Arg Val Ala Asp Thr Leu Tyr Lys Glu Lys Asp Thr Tyr Thr
                515                 520                 525

Asn Ala Lys Gly Lys Leu Lys Asn Met Ile Asn Ser Ile Leu Ile Glu
530                 535                 540

Ser Val Lys Ile
545

<210> SEQ ID NO 3
<211> LENGTH: 2024
<212> TYPE: DNA
<213> ORGANISM: Lycopersicon esculentum
<220> FEATURE:
<221> NAME/KEY: CDS
<222> LOCATION: (32)..(1678)

<400> SEQUENCE: 3
aaaaaaagcc aaaccttaga acaaacaagc a atg gct gct tct tct gct gat        52
                                   Met Ala Ala Ser Ser Ala Asp
                                    1               5
```

-continued

```
aag tgt cgc ccc ttg gct aat ttt cac cca tct gtt tgg gga tat cat      100
Lys Cys Arg Pro Leu Ala Asn Phe His Pro Ser Val Trp Gly Tyr His
     10                  15                  20 ttc ctt tct tat act cat gaa att act aat caa gaa aaa gtt gaa gtt      148
Phe Leu Ser Tyr Thr His Glu Ile Thr Asn Gln Glu Lys Val Glu Val
 25                  30                  35 gat gag tac aaa gag aca att aga aaa atg ctg gtg gaa act tgc gac      196
Asp Glu Tyr Lys Glu Thr Ile Arg Lys Met Leu Val Glu Thr Cys Asp
 40                  45                  50                  55 aat agc act caa aag ctt gtg ttg ata gac gcg atg caa cga ttg gga      244
Asn Ser Thr Gln Lys Leu Val Leu Ile Asp Ala Met Gln Arg Leu Gly
                 60                  65                  70 gtg gct tat cat ttc gat aat gaa att gaa aca tcc att caa aac att      292
Val Ala Tyr His Phe Asp Asn Glu Ile Glu Thr Ser Ile Gln Asn Ile
             75                  80                  85 ttt gat gca tcg tcc aaa cag aat gat aat gac aac aac ctt tac gtt      340
Phe Asp Ala Ser Ser Lys Gln Asn Asp Asn Asp Asn Asn Leu Tyr Val
         90                  95                 100 gtg tct ctt cgt ttt cga ctt gtg agg caa caa ggc cat tac atg tct      388
Val Ser Leu Arg Phe Arg Leu Val Arg Gln Gln Gly His Tyr Met Ser
    105                 110                 115 tca gat gtg ttc aag caa ttc acc aac caa gat ggg aaa ttc aag gaa      436
Ser Asp Val Phe Lys Gln Phe Thr Asn Gln Asp Gly Lys Phe Lys Glu
120                 125                 130                 135 aca ctt act aat gat gtc caa gga tta ttg agt ttg tat gaa gca tca      484
Thr Leu Thr Asn Asp Val Gln Gly Leu Leu Ser Leu Tyr Glu Ala Ser
                140                 145                 150 cat ctg aga gtg cgt aat gag gag att ctt gaa gaa gct ctt aca ttt      532
His Leu Arg Val Arg Asn Glu Glu Ile Leu Glu Glu Ala Leu Thr Phe
            155                 160                 165 acc acc act cat ctc gag tct att gtc tcc aac ttg agc aat aat aat      580
Thr Thr Thr His Leu Glu Ser Ile Val Ser Asn Leu Ser Asn Asn Asn
        170                 175                 180 aac tct ctt aag gtt gaa gtt ggt gaa gcc tta act cag cct att cgc      628
Asn Ser Leu Lys Val Glu Val Gly Glu Ala Leu Thr Gln Pro Ile Arg
    185                 190                 195 atg act tta cca agg atg gga gct aga aaa tac ata tcc att tac gaa      676
Met Thr Leu Pro Arg Met Gly Ala Arg Lys Tyr Ile Ser Ile Tyr Glu
200                 205                 210                 215 aac aat gat gca cac cac cat ttg ctt ttg aaa ttt gct aaa ttg gat      724
Asn Asn Asp Ala His His His Leu Leu Leu Lys Phe Ala Lys Leu Asp
                220                 225                 230 ttt aac atg ctg caa aag ttt cac caa aga gag ctt agt gat ctt aca      772
Phe Asn Met Leu Gln Lys Phe His Gln Arg Glu Leu Ser Asp Leu Thr
            235                 240                 245 agg tgg tgg aaa gat ttg gat ttt gca aat aaa tat cca tat gca aga      820
Arg Trp Trp Lys Asp Leu Asp Phe Ala Asn Lys Tyr Pro Tyr Ala Arg
        250                 255                 260 gac agg ttg gtt gag tgt tac ttc tgg ata tta gga gtg tat ttt gag      868
Asp Arg Leu Val Glu Cys Tyr Phe Trp Ile Leu Gly Val Tyr Phe Glu
    265                 270                 275 cca aaa tat agt cgt gcg aga aaa atg atg aca aaa gta ctc aac ctg      916
Pro Lys Tyr Ser Arg Ala Arg Lys Met Met Thr Lys Val Leu Asn Leu
280                 285                 290                 295 acc tcc att att gac gac act ttt gat gct tat gca acc ttt gac gaa      964
Thr Ser Ile Ile Asp Asp Thr Phe Asp Ala Tyr Ala Thr Phe Asp Glu
                300                 305                 310 ctt gtg act ttc aat gat gca atc cag aga tgg gat gct aat gca att     1012
Leu Val Thr Phe Asn Asp Ala Ile Gln Arg Trp Asp Ala Asn Ala Ile
```

-continued

```
                  315                 320                 325
gat tca ata caa cca tat atg aga cct gct tat caa gct ctt cta gac      1060
Asp Ser Ile Gln Pro Tyr Met Arg Pro Ala Tyr Gln Ala Leu Leu Asp
        330                 335                 340 att tac agt gaa atg gaa caa gtg ttg tcc aaa gaa ggt aaa ctg gac      1108
Ile Tyr Ser Glu Met Glu Gln Val Leu Ser Lys Glu Gly Lys Leu Asp
345                 350                 355 cgt gta tac tat gca aaa aat gag atg aaa aag ttg gtg aga gcc tat      1156
Arg Val Tyr Tyr Ala Lys Asn Glu Met Lys Lys Leu Val Arg Ala Tyr
360                 365                 370                 375 ttt aag gaa acc caa tgg ttg aat gat tgt gac cat att cca aaa tat      1204
Phe Lys Glu Thr Gln Trp Leu Asn Asp Cys Asp His Ile Pro Lys Tyr
            380                 385                 390 gag gaa caa gtg gag aat gca atc gta agt gct ggc tat atg atg ata      1252
Glu Glu Gln Val Glu Asn Ala Ile Val Ser Ala Gly Tyr Met Met Ile
        395                 400                 405 tca aca act tgc ttg gtc ggt ata gaa gaa ttt ata tcc cac gag act      1300
Ser Thr Thr Cys Leu Val Gly Ile Glu Glu Phe Ile Ser His Glu Thr
    410                 415                 420 ttt gaa tgg ttg atg aat gag tct gtg att gtt cga gct tcc gca ttg      1348
Phe Glu Trp Leu Met Asn Glu Ser Val Ile Val Arg Ala Ser Ala Leu
425                 430                 435 att gcc aga gca atg aac gat att gtt gga cat gaa gat gaa caa gaa      1396
Ile Ala Arg Ala Met Asn Asp Ile Val Gly His Glu Asp Glu Gln Glu
440                 445                 450                 455 aga gga cat gta gct tca ctt att gaa tgt tac atg aaa gat tat gga      1444
Arg Gly His Val Ala Ser Leu Ile Glu Cys Tyr Met Lys Asp Tyr Gly
            460                 465                 470 gct tca aag caa gag act tac att aag ttc ctg aaa gag gtc acc aat      1492
Ala Ser Lys Gln Glu Thr Tyr Ile Lys Phe Leu Lys Glu Val Thr Asn
        475                 480                 485 gca tgg aag gac ata aac aaa caa ttc tcc cgt cca act gaa gta cca      1540
Ala Trp Lys Asp Ile Asn Lys Gln Phe Ser Arg Pro Thr Glu Val Pro
    490                 495                 500 atg ttt gtc ctt gaa cga gtt cta aat ttg aca cgt gtg gct gac acg      1588
Met Phe Val Leu Glu Arg Val Leu Asn Leu Thr Arg Val Ala Asp Thr
505                 510                 515 tta tat aag gag aaa gat aca tat tca acc gcc aaa gga aaa ctt aaa      1636
Leu Tyr Lys Glu Lys Asp Thr Tyr Ser Thr Ala Lys Gly Lys Leu Lys
520                 525                 530                 535 aac atg att aat cca ata cta att gaa tct gtc aaa ata taa              1678
Asn Met Ile Asn Pro Ile Leu Ile Glu Ser Val Lys Ile
            540                 545 atataatgct gaaattgcac cttcatcatc caactattca cagcaaaata aggcatataa    1738
taaattgaag actcacaaca tatgagttgt taattcctgg gatgtttgaa ataaacaata    1798
attgttttta tttaatttgc taagccaaag tgaaatatac aacacttgag ttgtattaaa    1858
tcatgtttta tctcatttcc agcttgtgag tttggattat tatattgtta attatcatca    1918
ctttataatg tactgtaatc gtattgtatt tgtattgtag tgttgtcata ataaatttg     1978 aataaaatat atttttgttt caattccaaa aaaaaaaaaa aaaaaa                   2024
```

<210> SEQ ID NO 4
<211> LENGTH: 548
<212> TYPE: PRT
<213> ORGANISM: Lycopersicon esculentum

<400> SEQUENCE: 4

Met Ala Ala Ser Ser Ala Asp Lys Cys Arg Pro Leu Ala Asn Phe His

-continued

```
  1               5                    10                   15
Pro Ser Val Trp Gly Tyr His Phe Leu Ser Tyr Thr His Glu Ile Thr
                20                  25                  30

Asn Gln Glu Lys Val Glu Val Asp Glu Tyr Lys Glu Thr Ile Arg Lys
            35                  40                  45

Met Leu Val Glu Thr Cys Asp Asn Ser Thr Gln Lys Leu Val Leu Ile
        50                  55                  60

Asp Ala Met Gln Arg Leu Gly Val Ala Tyr His Phe Asp Asn Glu Ile
65                  70                  75                  80

Glu Thr Ser Ile Gln Asn Ile Phe Asp Ala Ser Ser Lys Gln Asn Asp
                85                  90                  95

Asn Asp Asn Asn Leu Tyr Val Val Ser Leu Arg Phe Arg Leu Val Arg
            100                 105                 110

Gln Gln Gly His Tyr Met Ser Ser Asp Val Phe Lys Gln Phe Thr Asn
        115                 120                 125

Gln Asp Gly Lys Phe Lys Glu Thr Leu Thr Asn Asp Val Gln Gly Leu
130                 135                 140

Leu Ser Leu Tyr Glu Ala Ser His Leu Arg Val Arg Asn Glu Glu Ile
145                 150                 155                 160

Leu Glu Glu Ala Leu Thr Phe Thr Thr Thr His Leu Glu Ser Ile Val
                165                 170                 175

Ser Asn Leu Ser Asn Asn Asn Ser Leu Lys Val Glu Val Gly Glu
            180                 185                 190

Ala Leu Thr Gln Pro Ile Arg Met Thr Leu Pro Arg Met Gly Ala Arg
        195                 200                 205

Lys Tyr Ile Ser Ile Tyr Glu Asn Asn Asp Ala His His His Leu Leu
210                 215                 220

Leu Lys Phe Ala Lys Leu Asp Phe Asn Met Leu Gln Lys Phe His Gln
225                 230                 235                 240

Arg Glu Leu Ser Asp Leu Thr Arg Trp Trp Lys Asp Leu Asp Phe Ala
                245                 250                 255

Asn Lys Tyr Pro Tyr Ala Arg Asp Arg Leu Val Glu Cys Tyr Phe Trp
            260                 265                 270

Ile Leu Gly Val Tyr Phe Glu Pro Lys Tyr Ser Arg Ala Arg Lys Met
        275                 280                 285

Met Thr Lys Val Leu Asn Leu Thr Ser Ile Ile Asp Asp Thr Phe Asp
290                 295                 300

Ala Tyr Ala Thr Phe Asp Glu Leu Val Thr Phe Asn Asp Ala Ile Gln
305                 310                 315                 320

Arg Trp Asp Ala Asn Ala Ile Asp Ser Ile Gln Pro Tyr Met Arg Pro
                325                 330                 335

Ala Tyr Gln Ala Leu Leu Asp Ile Tyr Ser Glu Met Glu Gln Val Leu
            340                 345                 350

Ser Lys Glu Gly Lys Leu Asp Arg Val Tyr Tyr Ala Lys Asn Glu Met
        355                 360                 365

Lys Lys Leu Val Arg Ala Tyr Phe Lys Glu Thr Gln Trp Leu Asn Asp
370                 375                 380

Cys Asp His Ile Pro Lys Tyr Glu Glu Gln Val Glu Asn Ala Ile Val
385                 390                 395                 400

Ser Ala Gly Tyr Met Met Ile Ser Thr Thr Cys Leu Val Gly Ile Glu
                405                 410                 415

Glu Phe Ile Ser His Glu Thr Phe Glu Trp Leu Met Asn Glu Ser Val
            420                 425                 430
```

```
Ile Val Arg Ala Ser Ala Leu Ile Ala Arg Ala Met Asn Asp Ile Val
        435                 440                 445

Gly His Glu Asp Glu Gln Glu Arg Gly His Val Ala Ser Leu Ile Glu
        450                 455                 460

Cys Tyr Met Lys Asp Tyr Gly Ala Ser Lys Gln Glu Thr Tyr Ile Lys
465                 470                 475                 480

Phe Leu Lys Glu Val Thr Asn Ala Trp Lys Asp Ile Asn Lys Gln Phe
                485                 490                 495

Ser Arg Pro Thr Glu Val Pro Met Phe Val Leu Glu Arg Val Leu Asn
            500                 505                 510

Leu Thr Arg Val Ala Asp Thr Leu Tyr Lys Glu Lys Asp Thr Tyr Ser
        515                 520                 525

Thr Ala Lys Gly Lys Leu Lys Asn Met Ile Asn Pro Ile Leu Ile Glu
    530                 535                 540

Ser Val Lys Ile
545

<210> SEQ ID NO 5
<211> LENGTH: 17
<212> TYPE: DNA
<213> ORGANISM: Artificial Sequence
<220> FEATURE:
<221> NAME/KEY: modified_base
<222> LOCATION: (3)
<223> OTHER INFORMATION: n  at position 3  is an inosine
<221> NAME/KEY: modified_base
<222> LOCATION: (6)
<223> OTHER INFORMATION: n at position 6 is an inosine
<223> OTHER INFORMATION: Description of Artificial Sequence: forward
      primer

<400> SEQUENCE: 5
ranggnrart tyaarga                                                        17

<210> SEQ ID NO 6
<211> LENGTH: 18
<212> TYPE: DNA
<213> ORGANISM: Artificial Sequence
<220> FEATURE:
<221> NAME/KEY: modified_base
<222> LOCATION: (13)
<223> OTHER INFORMATION: n at position 13 is an inosine
<221> NAME/KEY: modified_base
<222> LOCATION: (16)
<223> OTHER INFORMATION: n at position 16 is an inosine
<223> OTHER INFORMATION: Description of Artificial Sequence: reverse
      primer

<400> SEQUENCE: 6
ytkcatrtar tcngrnag                                                       18
```